US008786241B2

(12) United States Patent
Nowlin et al.

(10) Patent No.: US 8,786,241 B2
(45) Date of Patent: *Jul. 22, 2014

(54) SOFTWARE CENTER AND HIGHLY CONFIGURABLE ROBOTIC SYSTEMS FOR SURGERY AND OTHER USES

(75) Inventors: William C. Nowlin, Los Altos, CA (US); Paul W. Mohr, Mountain View, CA (US); Bruce M. Schena, Menlo Park, CA (US); David Q. Larkin, Menlo Park, CA (US); Gary S. Guthart, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/175,458

(22) Filed: Jul. 1, 2011

(65) Prior Publication Data
US 2011/0264108 A1 Oct. 27, 2011

Related U.S. Application Data

(63) Continuation of application No. 11/133,423, filed on May 19, 2005, now Pat. No. 8,004,229.

(51) Int. Cl.
*B25J 15/02* (2006.01)

(52) U.S. Cl.
USPC ............ 318/568.21; 318/568.11; 318/568.13; 318/568.18; 318/568.2

(58) Field of Classification Search
USPC .............. 318/560, 567, 568.1, 568.11, 568.2, 318/568.21
See application file for complete search history.

(56) References Cited

U.S. PATENT DOCUMENTS

| 3,920,972 | A | 11/1975 | Corwin, Jr. et al. |
| 4,028,533 | A | 6/1977 | Matsubara |
| 4,063,073 | A | 12/1977 | Strayer |
| 4,578,757 | A | 3/1986 | Stark |
| 4,999,553 | A | 3/1991 | Seraji |
| 5,130,632 | A | 7/1992 | Ezawa et al. |
| 5,430,543 | A | 7/1995 | Howard |
| 5,513,100 | A | 4/1996 | Parker et al. |
| 5,587,937 | A | 12/1996 | Massie et al. |

(Continued)

FOREIGN PATENT DOCUMENTS

| EP | 1234641 A1 | 8/2002 |
| GB | 2311149 A | 9/1997 |

(Continued)

OTHER PUBLICATIONS

Baerlocher, P. et al., "Task Priority Formulations for the Kinematic Control of Highly Redundant Articulated Structures," IEEE/RSJ International Conference on Intelligent Robots and Systems, 1998, pp. 323-329, vol. 1, IEEE.

(Continued)

*Primary Examiner* — Kawing Chan

(57) ABSTRACT

Telerobotic, telesurgical, and/or surgical robotic devices, systems, and methods employ surgical robotic linkages that may have more degrees of freedom than an associated surgical end effector n space. A processor can calculate a tool motion that includes pivoting of the tool about an aperture site. Linkages movable along a range of configurations for a given end effector position may be driven toward configurations which inhibit collisions. Refined robotic linkages and method for their use are also provided.

22 Claims, 27 Drawing Sheets

(56) References Cited

U.S. PATENT DOCUMENTS

| | | | |
|---|---|---|---|
| 5,632,758 A | 5/1997 | Sklar | |
| 5,710,870 A | 1/1998 | Ohm et al. | |
| 5,737,500 A | 4/1998 | Seraji et al. | |
| 5,823,980 A * | 10/1998 | Kopfer | 602/21 |
| 5,855,583 A | 1/1999 | Wang et al. | |
| 5,908,458 A | 6/1999 | Rowe et al. | |
| 6,037,927 A | 3/2000 | Rosenberg | |
| 6,098,260 A | 8/2000 | Sarh | |
| 6,246,200 B1 | 6/2001 | Blumenkranz et al. | |
| 6,312,435 B1 | 11/2001 | Wallace et al. | |
| 6,317,651 B1 | 11/2001 | Gerstenberger et al. | |
| 6,331,181 B1 | 12/2001 | Tierney et al. | |
| 6,377,011 B1 | 4/2002 | Ben-Ur | |
| 6,379,073 B1 | 4/2002 | Yoo et al. | |
| 6,400,115 B1 | 6/2002 | Yamazoe | |
| 6,424,885 B1 | 7/2002 | Niemeyer et al. | |
| 6,459,926 B1 * | 10/2002 | Nowlin et al. | 600/429 |
| 6,468,265 B1 | 10/2002 | Evans et al. | |
| 6,493,608 B1 | 12/2002 | Niemeyer | |
| 6,645,196 B1 | 11/2003 | Nixon et al. | |
| 6,678,582 B2 | 1/2004 | Waled | |
| 6,699,177 B1 | 3/2004 | Wang et al. | |
| 6,763,286 B2 | 7/2004 | Metelski | |
| 6,786,896 B1 | 9/2004 | Madhani et al. | |
| 7,083,571 B2 | 8/2006 | Wang et al. | |
| 7,280,633 B2 | 10/2007 | Cheng et al. | |
| 7,379,533 B2 | 5/2008 | Koertge | |
| 7,428,296 B2 | 9/2008 | Bernhardt et al. | |
| 7,564,949 B2 | 7/2009 | Sattler et al. | |
| 7,763,015 B2 | 7/2010 | Cooper et al. | |
| 8,004,229 B2 | 8/2011 | Nowlin et al. | |
| 8,041,459 B2 | 10/2011 | Sutherland et al. | |
| 2001/0013764 A1 | 8/2001 | Blumenkranz et al. | |
| 2001/0018591 A1 | 8/2001 | Brock et al. | |
| 2002/0082612 A1 | 6/2002 | Moll et al. | |
| 2002/0111713 A1 | 8/2002 | Wang et al. | |
| 2002/0120363 A1 | 8/2002 | Salisbury et al. | |
| 2003/0018412 A1 * | 1/2003 | Kimura | 700/245 |
| 2003/0060927 A1 * | 3/2003 | Gerbi et al. | 700/245 |
| 2003/0065311 A1 | 4/2003 | Wang et al. | |
| 2003/0109780 A1 | 6/2003 | Coste-Maniere et al. | |
| 2003/0139753 A1 | 7/2003 | Wang et al. | |
| 2003/0216715 A1 * | 11/2003 | Moll et al. | 606/1 |
| 2004/0034283 A1 | 2/2004 | Quaid, III | |
| 2004/0039485 A1 | 2/2004 | Niemeyer et al. | |
| 2004/0042583 A1 | 3/2004 | Wackerle et al. | |
| 2004/0111183 A1 | 6/2004 | Sutherland et al. | |
| 2004/0186484 A1 | 9/2004 | Ryan | |
| 2005/0104549 A1 | 5/2005 | Nishimura et al. | |
| 2006/0167440 A1 | 7/2006 | Cooper et al. | |
| 2007/0013336 A1 | 1/2007 | Nowlin et al. | |
| 2008/0037712 A1 | 2/2008 | Klingenbeck-Regn | |
| 2009/0234444 A1 | 9/2009 | Maschke | |
| 2009/0297011 A1 | 12/2009 | Brunner et al. | |
| 2010/0191371 A1 | 7/2010 | Hornung et al. | |
| 2011/0218679 A1 | 9/2011 | Cheng et al. | |
| 2011/0264109 A1 | 10/2011 | Nowlin et al. | |
| 2011/0264110 A1 * | 10/2011 | Nowlin et al. | 606/130 |
| 2011/0264111 A1 | 10/2011 | Nowlin et al. | |
| 2011/0264112 A1 | 10/2011 | Nowlin et al. | |
| 2011/0270271 A1 | 11/2011 | Nowlin et al. | |
| 2011/0276059 A1 | 11/2011 | Nowlin et al. | |

FOREIGN PATENT DOCUMENTS

| | | | | |
|---|---|---|---|---|
| JP | 2003159674 A * | 6/2003 | | B25J 5/00 |
| WO | WO 9729690 | 8/1997 | | |
| WO | 9950721 | 10/1999 | | |
| WO | WO02051329 A1 | 7/2002 | | |
| WO | WO-02060653 A9 | 12/2002 | | |

OTHER PUBLICATIONS

Boyd, Stephen, "Convex Optimization," 2004, 8 pages, Cambridge University Press.

English, James D. et al., "On the Implementation of Velocity Control for Kinematically Redundant Manipulators," IEEE transactions on systems, man, and cybernetics. Part A, Systems and humans, 2000, pp. 618-621, vol. 30—No. 3, IEEE.

Espiau, Bernard et al., "Collision Avoidance for Redundant Robots with Proximity Sensors," The Third International Symposium of Robotics Research, 1986, pp. 243-251, MIT Press.

Interlink Electronics, "Force Sensing Resistors for Medical Equipment, Automotive, and Musical Instruments," 2003, 1 page, Internet: http://www.interlinkelec.com/products/fsr/fsr.htm (last visited Jul. 2003).

Maciejewski, Anthony A. et al., "The Singular Value Decomposition: Computation and Applications to Robotics," The International Journal of Robotics Research, 1989, pp. 63-79, vol. 8—No. 6, SAGE Publications.

PCT/US06/17843 International Search Report, mailed Jan. 4, 2007, 6 pages.

PCT/US06/17843 Written Opinion of the International Search Authority, mailed Jan. 4, 2007, 9 pages.

Siciliano, Bruno et al., "A General Framework for Managing Multiple Tasks in Highly Redundant Robotic Systems," Fifth International Conference of Advanced Robotics, 1991, pp. 1211-1216, IEEE.

Smalley, Eric, "Flexible sensors make robot skin," Technology Research News, Sep. 22/29, 2004, 3 pages, Internet: http://www.trnmag.com/Stories/2004/092204/Flexible_sensors_make_robot_skin%20_092204.html (last visited Dec. 17, 2004).

Stanford University, Dexterous Manipulation Laboratory, "The 'Capaciflector' Proximity Sensor", 2005, 3 pages. Internet: http://www.cdr.stanford.edu/Touch/previous_projects/capaciflector/capaciflector.htm (last visited Jan. 5, 2005).

Tapeswitch Corporation, Data Sheet for Controflex Ribbon Switches, last downloaded Dec. 17, 2004, 2 pages, Internet: http://www.tapeswitch.com/nroducts/contflex,php.

Vertut, Jean and Phillipe Coiffet, *Robot Technology: Teleoperation and Robotics Evolution and Development*, English translation, Prentice-Hall, Inc., Inglewood Cliffs, NJ, USA 1986, vol. 3A, 332 pages.

Extended EP Search Report and Written Opinion for Application No. EP10196669.5, mailed Jul. 26, 2012, 7 pages.

Extended European Search Report and Written Opinion for Application No. EP10196664.6, mailed on Jul. 25, 2012, 7 pages.

Extended European Search Report and Written Opinion for Application No. EP101996666.1, mailed on Jul. 19, 2012, 7 pages.

European Search Report for Application No. EP10196665.3, mailed on Oct. 15, 2012, 8 pages.

European Search Report for Application No. EP10196670, mailed Oct. 26, 2012, 9 pages.

Nakamura Y., et al., "Task-Priority Based Redundancy Control of Robot Manipulators," International Journal of Robotics Research, Sage Science Press, Thousand Oaks, US, Jun. 21, 1987, vol. 6 (2), pp. 3-15.

European Search Report for Application No. EP10196671, mailed on Oct. 15, 2012, 7 pages.

Final Office Action mailed Dec. 19, 2012 for U.S. Appl. No. 13/175,477, filed Jul. 1, 2011.

Final Office Action mailed Dec. 19, 2012 for U.S. Appl. No. 13/175,572, filed Jul. 1, 2011.

Final Office Action mailed Dec. 20, 2012 for U.S. Appl. No. 13/175,550, filed Jul. 1, 2011.

Non-Final Office Action mailed Aug. 15, 2012 for U.S. Appl. No. 13/175,550, filed Jul. 1, 2011.

Non-Final Office Action mailed Jul. 19, 2012 for U.S. Appl. No. 13/175,477, filed Jul. 1, 2011.

Non-Final Office Action mailed Jul. 19, 2012 for U.S. Appl. No. 13/175,590, filed Jul. 1, 2011.

Non-Final Office Action mailed Mar. 28, 2013 for U.S. Appl. No. 13/175,498, filed Jul. 1, 2011.

Non-Final Office Action mailed Jan. 30, 2013 for U.S. Appl. No. 13/175,590, filed Jul. 1, 2011.

Non-Final Office Action mailed Jul. 31, 2012 for U.S. Appl. No. 13/175,572, filed Jul. 1, 2011.

(56) References Cited

OTHER PUBLICATIONS

Albu-Schaffer A., et al., "Cartesian Impedance Control Techniques for Torque Controlled Light-Weight Robots," Proceedings of the 2002 IEEE, International Conference on Robotics and Automation, 2002, pp. 657-663.

Albu-Schaffer A., et al., "Parameter Identification and Passivity Based Joint Control for a 7DOF Torque Controlled Light Weight Robot," Proceedings of the 2001 IEEE, International Conference on Robotics and Automation, 2001, vol. 3, pp. 2852-2858.

Da Vinci, Chirurgie-System Benutzerhandbuch, Intuitive Surgical Inc., 2004, 9 Chapters and 2 Appendixes, 260 pages.

Grunwald G., et al., "Programming by Touch: the Different Way of Human—Robot Interaction," IEEE Transactions on Industrial Electronics, 2003, vol. 50 (4), pp. 659-666.

Hirzinger G., et al., "A Mechatronics Approach to the Design of Light-Weight Arms and Multifingered Hands," Proceedings of the 2000 IEEE, International Conference on Robotics and Automation, 2000, pp. 46-54.

Hirzinger G., et al., "On a New Generation of Torque Controlled Light-Weight Robots," Proceedings of the 2001 IEEE, International Conference on Robotics and Automation, 2001, pp. 3356-3363.

Howe R.D., et al., "Robotics for Surgery," Annual Review of Biomedical Engineering, 1999, vol. 1, pp. 211-240.

Kazanzides, Peter et al., "Force Sensing and Control for a Surgical Robot," Int. Conference on Robotics and Automation, May 1992, Nice, France; pp. 612-617, vol. 1, IEEE.

Khatib O., "A Unified Approach for Motion and Force Control of Robot Manipulators: The Operational Space Formulation," IEEE Journa of Robotics and Automation, 1987, vol. Ra-3 (1), pp. 43-52.

Konietschke R., et al., "A Preoperative Planning Procedure for Robotically Assisted Minimally Invasive Interventions," Lecture Notes in Computer Science, CURAC, 2004.

Konietschke R., et al., "Manipulability and Accuracy Measures for a Medical Robot in Minimally Invasive Surgery," Conference Proceeding, In proceeding of: 9th International Symposium on Advances in Robot Kinematics(ARK), Sestri Levante, Italy, Jun. 28-Jul. 1, 2004, 8 pages.

Krupa A., et al., "Towards Semi-Autonomy in Laparoscopic Surgery Through Vision and Force Feedback Control," Experimental Robotics VII, Lecture Notes in Control and Information Sciences, 2001, vol. 271, pp. 189-198.

Maciejewski A.A., et al., "Obstacle Avoidance for Kinematically Redundant Manipulators in Dynamically Varying Environments," International Journal of Robotics Research, 1985, vol. 4 (3), pp. 109-117.

Michelin M., et al., "Dynamic Task/Posture Decoupling for Minimally Invasive Surgery Motions," Intelligent Robots and Systems, 2004, vol. 4, pp. 3625-3630.

Ortmaier T.J., "Motion Compensation in Minimally Invasive Robotic Surgery," 2002, 5 Chapters, 147 pages.

Schreiber G., "Interactive Redundant Robotics: Control of the Inverted Pendulum with Nullspace Motion," Proceedings of the 2001, IEEE/RSJ, International Conference on Intelligent Robots and Systems, 2001, pp. 158-164.

Schreiber G., Steuerung fur Redundante Robotersysteme: Benutzer and Aufgabenorientierte Verwendung Der Redundanz, 2004, 162 pages. (English Abstract).

Siciliano B., "Kinematic Control of Redundant Robot Manipulators: A Tutorial," Journal of Intelligent and Robotic Systems, 1990, vol. 3 (3), pp. 201-212.

Yigit S., et al., "Specific Combined Control Mechanisms for Human Robot Co-Operation," Institute for Process Control and Robotics (IPR), 2003, 6 pages.

Non-Final Office Action mailed Apr. 25, 2013 for U.S. Appl. No. 13/175,519 filed Jul. 1, 2011.

European Search Report for Application No. EP10196666, mailed on Jul. 19, 2012, 7 pages.

Final Office Action mailed Aug. 21, 2013 for U.S. Appl. No. 13/175,590, filed Jul. 1, 2011.

International Search Report and Written Opinion for Application No. PCT/US2006/017843, mailed on Jan. 4, 2007, 11 pages.

Non-Final Office Action mailed Jul. 3, 2013 for U.S. Appl. No. 13/175,550, filed Jul. 1, 2011.

Non-Final Office Action mailed Sep. 9, 2010 for U.S. Appl. No. 11/133,423, filed May 19, 2005.

Non-Final Office Action mailed Aug. 14, 2013 for U.S. Appl. No. 13/175,477, filed Jul. 1, 2011.

Notice of Allowance mailed Mar. 2, 2011 for U.S. Appl. No. 11/133,423, filed May 19, 2005.

Notice of Allowance mailed May 21, 2013 for U.S. Appl. No. 13/175,572, filed Jul. 1, 2011.

Notice of Allowance mailed Aug. 29, 2013 for U.S. Appl. No. 13/175,498, filed Jul. 1, 2011.

Schreiber G., Steuerung fur Redundante Robotersysteme: Benutzer und Aufgabenorientierte Verwendung Der Redundanz, 2004, 296 pages.

* cited by examiner

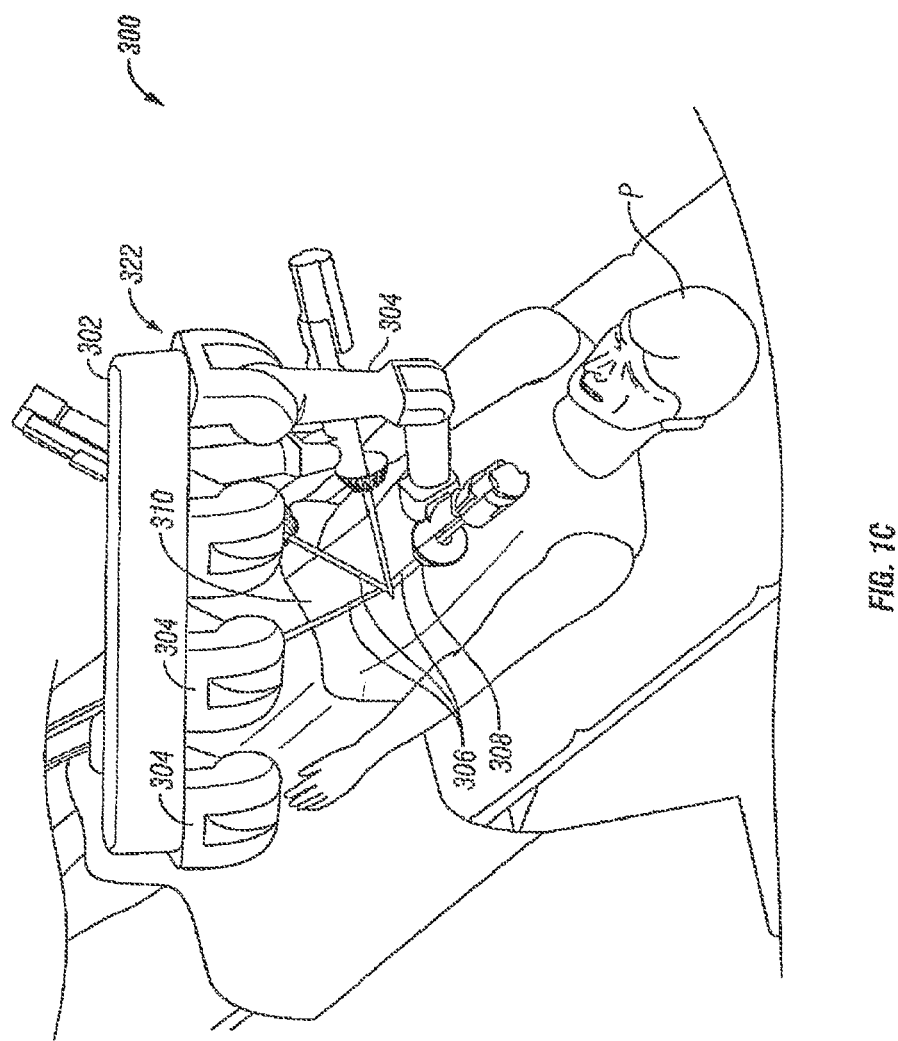

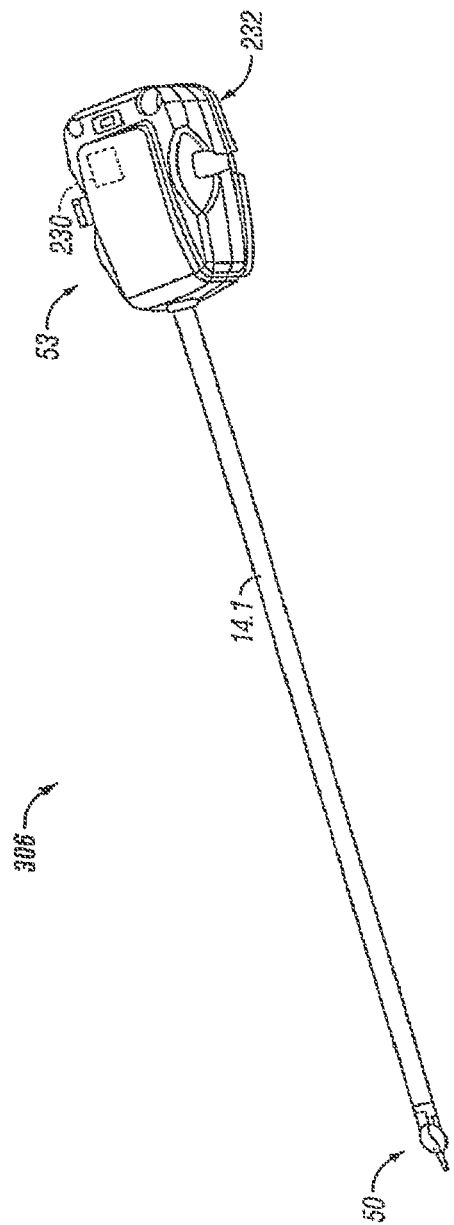

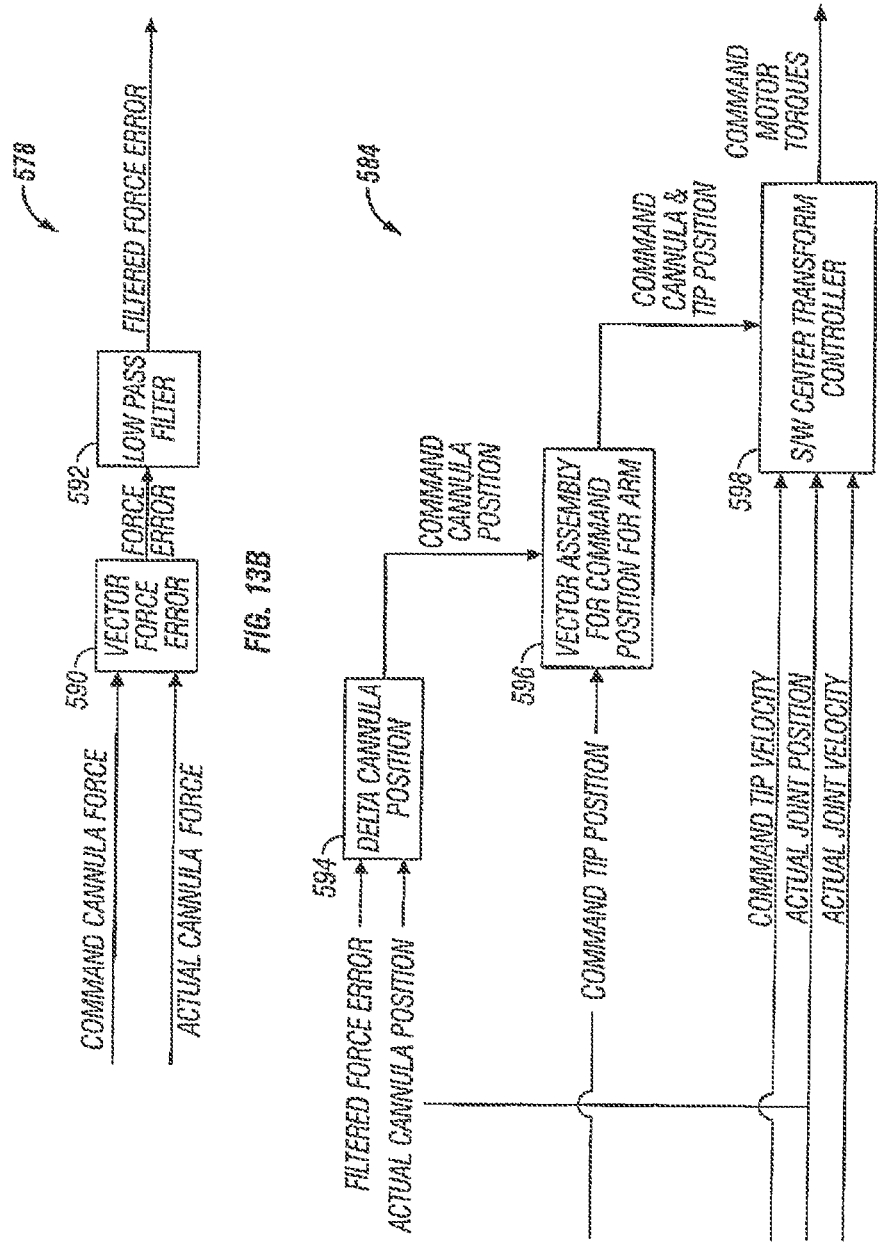

SOFTWARE CENTER AND HIGHLY CONFIGURABLE ROBOTIC SYSTEMS FOR SURGERY AND OTHER USES

CROSS-REFERENCES TO RELATED APPLICATIONS

The present application is a Continuation of U.S. application Ser. No. 11/133,423 filed May 19, 2005 (Allowed), the full disclosure of which is incorporated herein by reference in its entirety for all purposes.

STATEMENT AS TO RIGHTS TO INVENTIONS MADE UNDER FEDERALLY SPONSORED RESEARCH OR DEVELOPMENT

NOT APPLICABLE

BACKGROUND OF THE INVENTION

The present invention generally provides improved surgical and robotic devices, systems, and methods.

Minimally invasive medical techniques are aimed at reducing the amount of extraneous tissue which is damaged during diagnostic or surgical procedures, thereby reducing patient recovery time, discomfort, and deleterious side effects. Millions of surgeries are performed each year in the United States. Many of these surgeries can potentially be performed in a minimally invasive manner. However, only a relatively small number of surgeries currently use these techniques due to limitations in minimally invasive surgical instruments and techniques and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulators are included for moving an endoscope or other image capture device, additional surgical instruments, or the like.

While the new robotic surgical systems and devices have proven highly effective and advantageous, still further improvements would be desirable. For example, when moving the surgical instruments within a minimally invasive surgical site, robotic surgical manipulators may exhibit a significant amount of movement outside the patient, particularly when pivoting instruments about minimally invasive apertures. As the instruments may independently pivot about their associated apertures at the same time, the robotic manipulators disposed outside the patient may sometimes collide with each other (or with other structures or personnel). Additionally, set-up of the surgical robotic system in preparation for surgery can be challenging, and re-configuring the system to access different tissues of the patient during different phases of a procedure can be inconvenient.

For these and other reasons, it would be advantageous to provide improved devices, systems, and methods for surgery, robotic surgery, and other robotic applications. It would be particularly beneficial if these improved technologies provided a faster and easier set-up, and/or inhibited collisions of the robotic devices during use. Ideally, these improvements would be provided without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace. The present invention will often include a processor configured by software instructions to calculate a motion of the robotic linkage that includes pivoting a shaft of the manipulator linkage about an aperture site hence the notion of software centering. The joints of the robotic manipulators supporting the end effectors can allow the manipulator to move throughout a range of different configurations for a given end effector position, in some cases even when constraining lateral movement of the shaft from the aperture site so as to avoid injury to the adjacent tissues. The processor can take advantage of such manipulators to drive the manipulators to configurations which inhibit collisions involving one or more moving robotic structures. Set-up of such highly configurable robotic manipulators can be facilitated by processors which drive one or more joints of the manipulators while the manipulator is being positioned manually by the system operator (or by some other external interaction), with the joints optionally being driven in response to movements of other joints along the kinematic chain of the manipulator. Embodiments can adjust a center of pivotal motion of the manipulator in response to patient breathing and/or movement, in some cases by sensing forces applied between the manipulator and the tissues along the aperture site. Refined robotic structures for use in minimally invasive surgical applications and other applications are also provided, along with related robotic methods.

In one aspect of the present invention, a redundant degrees of freedom (RDOF) surgical robotic system with manipulate input is provided. The RDOF surgical robotic system comprises a manipulator assembly, an input device, and a processor. In response to a command to effect a desired movement of the end effector as received by the input device, the manipulator assembly manipulates a distal end effector relative to a proximal base. The manipulator has a plurality of joints providing sufficient degrees of freedom to allow a range of joint states for an end effector position. The processor couples the input device to the manipulator assembly and may be configured to operate in different modes. In the end effector manipulation mode, the processor determines movements of the joints in response to the command so as to move the end effector with the desired movement. In the clutch mode, the processor drives at least one of the joints in response to an external articulation of another joint of the manipulator assembly. The clutch mode may be a pose clutch mode, an instrument clutch mode, or a port clutch mode.

In another aspect of the present invention, a RDOF software centering surgical robotic system is provided. The RDOF software centering surgical robotic system comprises a processor, an input device, a manipulator, and a surgical instrument. The surgical instrument has a proximal end, a distal end effector suitable for insertion into a patient, and an intermediate portion therebetween. The manipulator supports the proximal end of the instrument and is therefore capable of moving/controlling the instrument from outside the patient. Between the manipulator and the instrument, there are a plurality of driven joints providing sufficient degrees of freedom to allow a range of joint states for an end effector position when the intermediate portion of the end effector passes through an access site. The input device receives a command to effect a desired end effector's movement. The processor couples the input device to the manipulator. In response to the commanded movement, the processor determines movements of the joints so that the intermediate portion of the instrument is within the access site during the end effector's desired movement.

In one embodiment, the movements of the joints as determined by the processor may also be designed to inhibit manipulator collision. In another embodiment, the movements of the joints as determined by the processor may be designed to drive the manipulator to desired combinations of joint states that achieve the underconstrained primary solution and a secondary control task. In yet another embodiment, the movements of the joints as determined by the processor may be designed to inhibit movement of a pivotal center of the intermediate portion of the instrument in response to a port stiffness factor. In yet another embodiment, the movements of the joints as determined by the processor comply with a priority task selected from a priority list. In yet another embodiment, the RDOF software centering surgical robotic system further include a sensor system to indicate to the processor a position of the access site and/or a reactive force between the intermediate portion of the instrument and the access site aperture.

In yet another aspect of the present invention, a multi-manipulator RDOF surgical robot with collision avoidance capability is provided. The multi-manipulator RDOF surgical robot comprises a first manipulator assembly, a second manipulator assembly, an input device, and a processor. The first manipulator assembly has a first end effector and a plurality of joint states for one first end effector position. The second manipulator assembly has a second end effector and has the capability to transmit state signals indicating movement of the second manipulator assembly. The input device receives an input for a first desired movement of the first end effector. The processor is coupled to the input, the first manipulator assembly, and the second manipulator assembly. The processor determines a movement of the first manipulator assembly in response to the input but with the second manipulator assembly state signals being taken into consideration so as to inhibit collisions between the manipulator assemblies. Using the determined movement, the processor controls the first end effector to effect the first desired movement.

In yet another aspect of the present invention, a surgical robotic manipulator with an upper arm roll is provided. The surgical robotic manipulator comprises a moveable surgical instrument holder, a base which is positionable near a workspace, and an arm assembly which is pivotally coupled between the base and instrument holder. The arm assembly includes a first link having a first axis, a second link having a second axis, a pivotal arm joint coupled between the first link and the second link to vary an angle between the first axis and the second axis, and a first roll joint between the base and the pivotal arm joint. The first roll joint has an arm roll axis extending along the first axis.

A further understanding of the nature and advantages of the present invention will become apparent by reference to the remaining portions of the specification and drawings.

BRIEF DESCRIPTION OF THE DRAWINGS

FIG. 1C is a perspective view schematically illustrating a surgical method performed at a minimally invasive surgical site within a patient using the manipulator assemblies and surgeon console of FIGS. 1A and 1B.

FIG. 3 is perspective view of an exemplary robotic surgical instrument or tool to be mounted on the manipulators of FIG. 1B.

FIGS. 8A-8D schematically illustrate different clutching modes for manually repositioning at least a portion of a robotic manipulator assembly to accommodate a new aperture position, to pivot an instrument holder about an aperture, to change a pose of the manipulator without moving the end effector or instrument holder, and the like.

FIGS. 13B and 13C schematically illustrate aspects of the control system of FIG. 13A.

DETAILED DESCRIPTION OF THE INVENTION

Figure 1A:
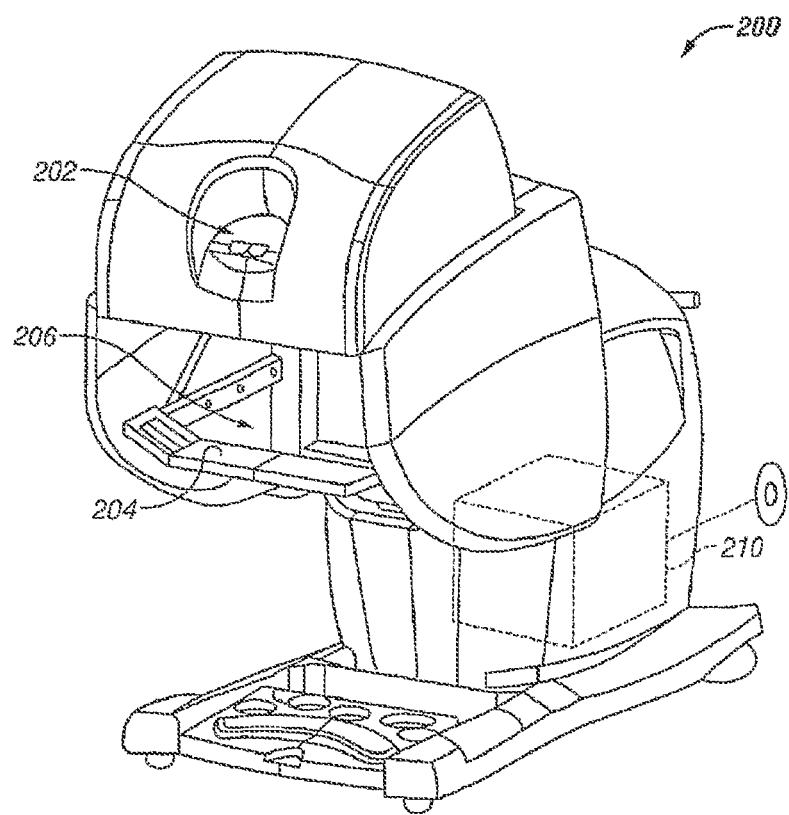
FIG. 1A is a perspective view illustrating a master surgeon console or workstation for inputting surgical procedure commands, the console including a processor for generating manipulator command signals in response to the input commands.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators so as to inhibit interference or collisions between these moving structures, and the like.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages which inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup. Hence, while the most immediate applications for the present invention may include telesurgical systems, the structures, devices, and systems described herein may also find applications in a wide variety of other telerobotic and robotic applications.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Hence, so long as the movements described are based on the associated calculations, the calculations of movements of the joints and movements of an end effector described herein may by performed using a position control algorithm, a velocity control algorithm, a combination of both, and/or the like.

Embodiments of the invention may include a processor which is configured to take advantage of the degrees of freedom of a manipulator structure for a plurality of tasks, goals, or purposes. When used with highly configurable manipulators, these processors may have joint controller programming instructions or code which allows them to derive generally suitable joint commands that could be used for one control task, such as moving the end effector to a desired position. However, as the manipulators may have more degrees of freedom than are needed to accomplish this task, the solution generated by the joint controller will often be underconstrained. In other words, one joint controller of the processor will often calculate a range of joint positions and/or relationships, any of which could result in the desired end effector position in space.

Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

When the solution calculated by a joint controller of the processor is underconstrained, the solution provided by that joint controller may represent a subset of the joint space. To identify what specific commands are to be transmitted to the joints of the manipulator when a primary solution is underconstrained, additional programming instructions or code of the processor may effectively act as a subspace filter, selecting a desirable manipulator state and specific set of joint commands from the range of alternatives generated by the joint controller. Advantageously, the selected commands can be used to serve a second goal, task, or function. For example, when a primary joint controller is implemented as a velocity controller, such a filter can identify a linear combination of joint velocities that are orthogonal to the function of the primary joint controller, with these additional velocities driving the manipulator so that it passes through an aperture, toward a desired high-dexterity pose, and/or to inhibit collisions. The filter will often be configuration-dependent, so that the joint commands selected by the filter will depend on the configuration or state of the joints, manipulator, and/or workspace. In fact, the primary joint controller may also effectively comprise a filter selecting the primary solution from the overall joint space based on an input command and/or the like.

As used herein the term "overconstrained" encompass robotic systems in which a task or tasks of one or more controller will, at least at times and if maintained as rigid constraints, be capable of exceeding the available degrees of freedom of an associated manipulator assembly.

As used herein, an "external" force or articulation of a robotic system includes forces of movement of the manipulator assembly which are applied by a system user or other person, a workspace or environment, an unintended collision with another structure, and the like; but generally does not encompass robotically calculated and intended forces and movements applied by driving the manipulator of the system.

As used herein, the term "null space" is defined as the subspace S of a vector input space for a linear operator (a matrix) M, such that for any vector x in S, M .x=0.

While the processor is often described herein as having a primary joint controller and/or a configuration-dependent filter, and/or as having a first module and a second module performing functions related to such a controller and filter, the processors described herein may also have a plurality of filters (optionally being three or more filters), three or more modules for three or more different control tasks, and the like. The processor will often define one or more priority between the tasks associated with these filters and modules, thereby assigning greater weight or importance to a higher priority task than a lower priority task. In many embodiments, even when a primary solution is underconstrained, the tasks associated with the joint controller and filter(s) may combine to overconstrain the system if such priorities were absent, so that the lower-priority tasks or goals may have little or no effect on at least some manipulator movements.

Referring to FIG. 1A of the drawings, an operator workstation or surgeon's console of a minimally invasive telesurgical system is generally indicated by reference numeral 200. The workstation 200 includes a viewer 202 where an image of a surgical site is displayed in use. A support 204 is provided on which an operator, typically a surgeon, can rest his or her forearms while gripping two master controls 220 (see FIG. 2), one in each hand. The master controls or input devices are positioned in a space 206 inwardly beyond the support 204. When using workstation 200, the surgeon typically sits in a chair in front of the workstation, positions his or her eyes in front of viewer 202 and grips the master controls, one in each hand, while resting his or her forearms on support 204. A processor 210 of the workstation generates signals in response to the motion of the input devices.

Figure 1B:
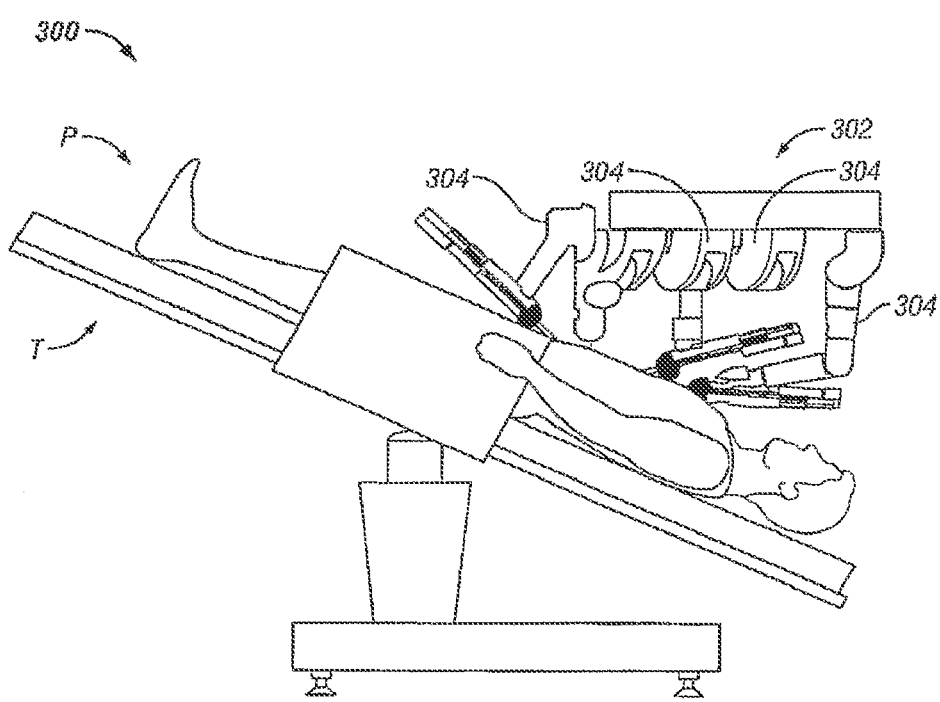
FIG. 1B is a side view schematically illustrating a surgical station having a plurality of robotic manipulators for robotically moving surgical instruments having surgical end effectors at an internal surgical site within a patient, and a method for performing a surgical procedure with the manipulator-instrument assemblies.

In FIG. 1B of the drawings, a surgical station is generally indicated by reference numeral 300. In use, a patient P is supported by a table T adjacent one or more manipulator support bases 302. Base 302 is generally supported from above, and may be ceiling mounted, supported by a wall of a room in which surgical station 300 is disposed, mounted to a surgical table, mounted to an arm of a cart having wheels or casters for moving the manipulators within the operating room or between operating rooms, or the like. The structure supporting base 302 is not shown. Base 302 will typically remain in a fixed location over patient P during at least a portion of a surgical procedure. The workstation 200 (see FIG. 1A) is typically positioned at some distance from the surgical station 300, optionally being separated by a few feet within an operating room. In other embodiments, surgical station 300 and workstation 200 may be separated by a significant distance, optionally being disposed in separate rooms or even different buildings.

Surgical station 300 typically includes a plurality of robotic manipulators 304, often having three or more robotic manipulators, with the exemplary embodiment including four robotic manipulators supported by base 302. Exemplary base 302 comprises an elongate base body supported in a horizontal orientation, with manipulators 304 being distributed horizontally along the length of the base. In other embodiments, a plurality of separately positionable bases may support the manipulators.

As can be seen in FIGS. 1B and 1C, each of the robotic manipulators supports an associated surgical instrument 306. One or more of the instruments may comprise an image capturing device 308 such as an endoscope or the like. Each of the other three manipulators 304 may support an instrument adapted for manipulating tissues at an internal surgical site 310. Endoscope 308 is operatively connected to viewer 202 to display an image captured at its viewing end on the viewer. Two of the other robotic manipulators 304 may each be operatively connected to one of the master controls, and a processor 210 may alter which manipulator is operatively connected with which master control. Thus, the movement of all the manipulators may be controlled by manipulation of the master controls. In some embodiments, additional input devices may be provided for use by another surgeon, a surgical assistant, or the like.

Figure 2:
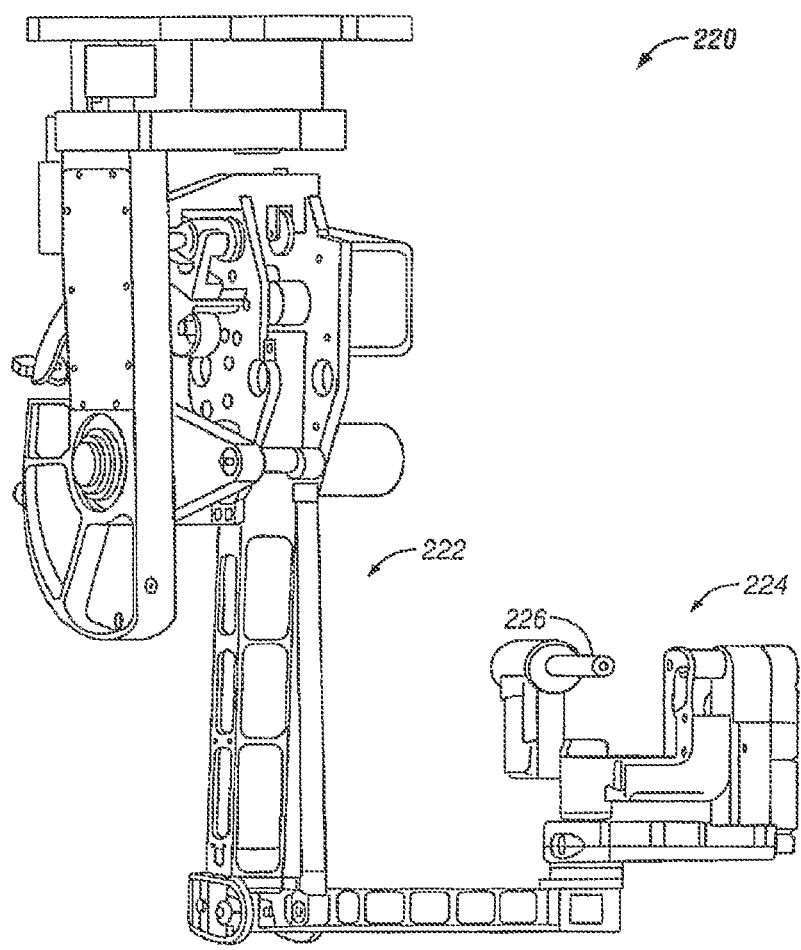
FIG. 2 is a side view illustrating a master controller input device having a handle for inputting a desired movement to the workstation of FIG. 1A.
Figure 3A:
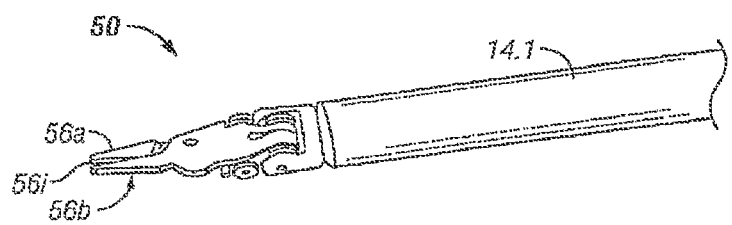
FIGS. 3A-3F are perspective views of a plurality of different end effectors for surgical instruments of different types.
Figure 3B:
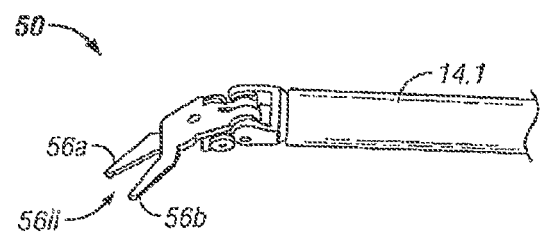
Figure 3C:
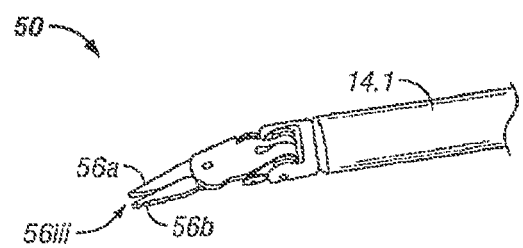
Figure 3D:
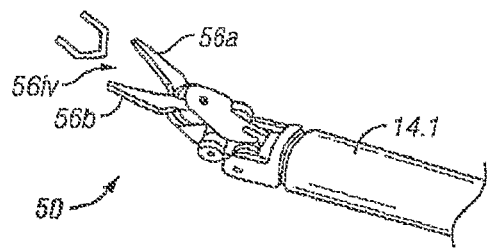
Figure 3E:
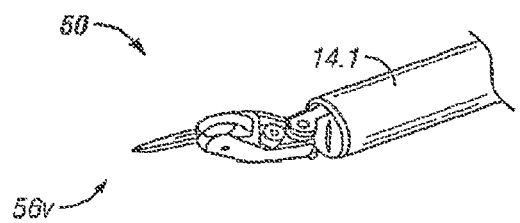
Figure 3F:
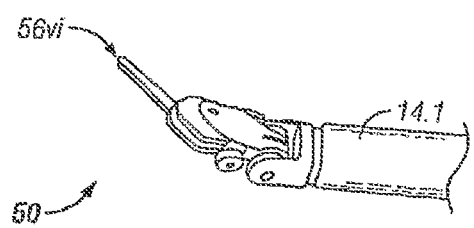

An exemplary input device 220 and surgical instrument 306 are illustrated in FIGS. 2 and 3, respectively. Input device 220 includes an arm 222 and a wrist 224 which together allow translational and orientational movement of an input handle 226 relative to the structure of workstation 200 (see FIG. 1A). Handle 222 will generally move with a plurality of degrees of freedom relative to the workstation structure, the exemplary input device 220 providing six degrees of freedom of movement of handle 226. The linkage supporting the handle may include more or less than six degrees of freedom. Grip members are movably coupled to handle 226 and the handle generates a grip signal indicating separation between the grip members.

Referring now to FIG. 3, surgical tool or instrument 306 generally includes a surgical end effector 50 supported relative to a housing 53 by an intermediate portion of the instrument, the intermediate portion often comprising of an elongate shaft 14.1. End effector 50 may be supported relative to the shaft by a distal joint or wrist so as to facilitate orienting the end effector within an internal surgical workspace. Proximal housing 53 will typically include an interface 232 adapted for coupling to a holder of a manipulator 304. As described in more detail in U.S. Pat. No. 6,331,181, the full disclosure of which is incorporated herein by reference, instrument 306 will often include a memory 230, with the memory typically being electrically coupled to a data interface (the data interface typically forming a portion of interface 232). This allows data communication between memory 230 and the robotic surgical processor 210 of workstation 200 (see FIG. 1A) when the instrument is mounted on the manipulator.

Referring now to FIGS. 3A-3F, a variety of alternative robotic surgical instruments of different types and differing end effectors 50 may be used, with the instruments of at least some of the manipulators being removed and replaced during a surgical procedure. Several of these end effectors, including DeBakey Forceps 56$i$, microforceps 56$ii$, Potts scissors 56$iii$, and clip a plier 56$iv$ include first and second end effector elements 56$a$, 56$b$ which pivot relative to each other so as to define a pair of end effector jaws. Other end effectors, including scalpel 56$v$ and electrocautery probe 56$vi$ have a single end effector element. For instruments having end effector jaws, the jaws will often be actuated by squeezing the grip members of handle 226. Single end effector instruments may also be actuated by gripping of the grip members, for example, so as to energize an electrocautery probe.

The elongate shafts 14.1 of instruments 306 allow the end effectors 50 and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instruments 306 about the location at which the shaft 14.1 passes through the minimally invasive aperture. In other words, manipulators 304 will move the proximal housing 53 outside the patient so that shaft 14.1 extends through a minimally invasive aperture location so as to help provide a desired movement of end effector 50. Hence, manipulators 304 will often undergo significant movement outside patient P during a surgical procedure.

An exemplary structure of manipulator 304 can be understood with reference to FIGS. 4A-4C, 5A and 5B, and FIG. 6. As described above, manipulator 304 generally supports an instrument 306 and effects movements of the instrument relative to a base 302. As a number of different instruments having differing end effectors may be sequentially mounted on each manipulator 304 during a surgical procedure (typically with the help of a surgical assistant), an instrument holder 320 will preferably allow rapid removal and replacement of the mounted instrument. The manipulator will often be covered by a sterile drape while the instrument may not be. An exemplary sterile adaptor and drape are described in U.S. Pat. No. 6,331,181. As can be understood with reference the FIGS. 1B and 1C, manipulators 304 are mounted to base 302 by a pivotal mounting joint 322 so as to allow the remainder of manipulator 304 to rotate about a first joint axis J1, with the first joint 322 providing rotation about a vertical axis in the exemplary embodiment. Base 302 and first joint 322 generally comprise a proximal portion of manipulator 304, with the manipulator extending distally from the base toward instrument holder 320 and end effector 50.

Figure 4A:
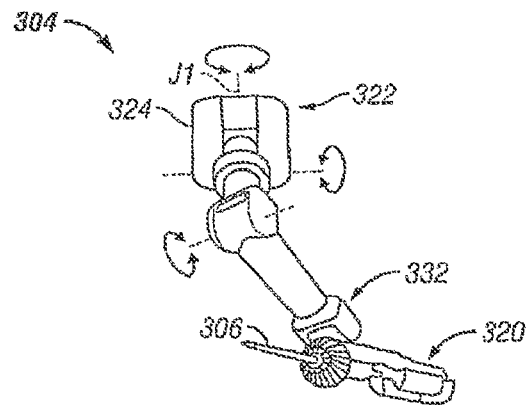
FIGS. 4A-4C are bottom, side, and back views of an exemplary robotic manipulator assembly having a range of joint states for a given end effector position.
Figure 4B:
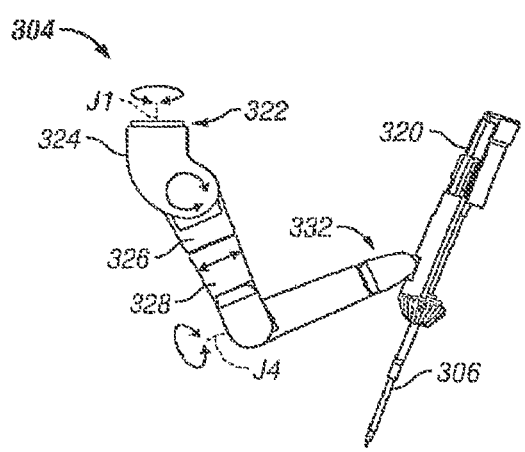
Figure 4C:
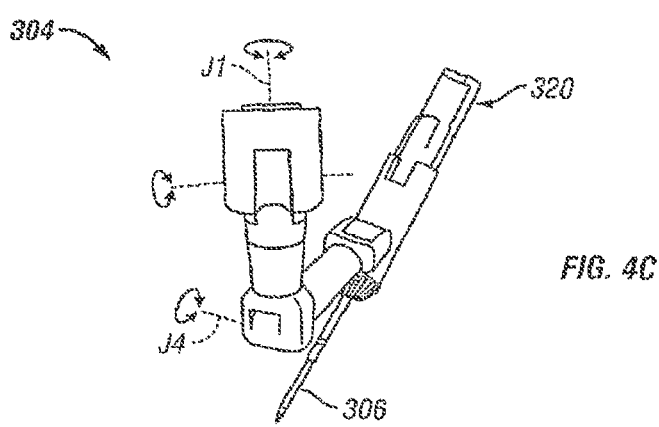
Figure 6:
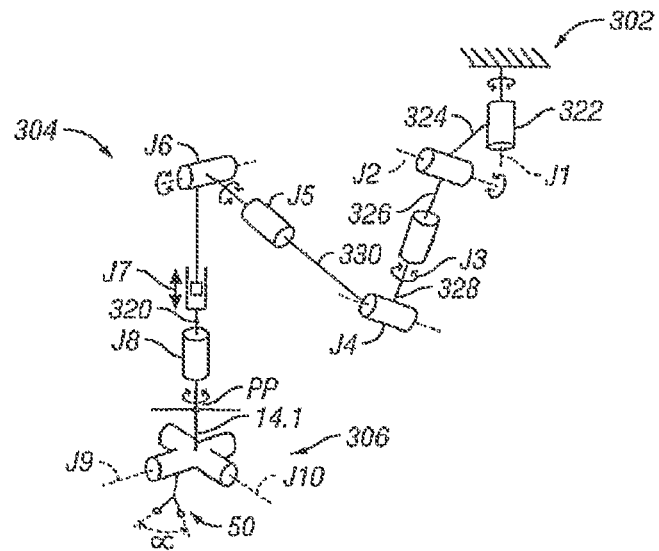
FIG. 6 schematically illustrates the degrees of freedom provided by the manipulator of FIGS. 4A-C and the instrument of FIG. 3 mounted thereon.

Describing the individual links of manipulator linkage 304 as illustrated in FIGS. 4A-C along with the axes of rotation of the joints connecting the links as illustrated in FIG. 6, a first link 324 extends distally from base 302 and rotates about first pivotal joint axis J1 at joint 322. Many of the remainder of the joints can be identified by their associated rotational axes in FIG. 6. For example, a distal end of first link 324 is coupled to a proximal end of a second link 326 at a joint providing a horizontal pivotal axis J2. A proximal end of a third link 328 is coupled to the distal end of the second link 326 at a roll joint so that the third link generally rotates or rolls at joint J3 about an axis extending along (and ideally aligned with) axes of both the second and third links. Proceeding distally, after another pivotal joint J4, the distal end of a fourth link 330 is coupled to instrument holder 320 by a pair of pivotal joints J5, J6 that together define an instrument holder wrist 332. A translational or prismatic joint J7 of the manipulator facilitates axial movement of instrument 306 through the minimally invasive aperture, and also facilitates attachment of the instrument holder to a cannula through which the instrument is slidably inserted.

Distally of instrument holder 320, instrument 306 may include additional degrees of freedom. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In other words, the interface between the instrument and manipulator may be disposed more proximally or distally along the kinematic chain of the manipulator assembly (which may include both the instrument and manipulator). In the exemplary embodiment, instrument 306 includes a rotational joint J8 proximally of the pivot point PP, which generally is disposed at the site of a minimally invasive aperture. A distal wrist of the instrument allows pivotal motion of end effector 50 about instrument wrist joint axes J9, J10. An angle α between end effector jaw elements may be controlled independently of the end effector location and orientation.

Figure 7A:
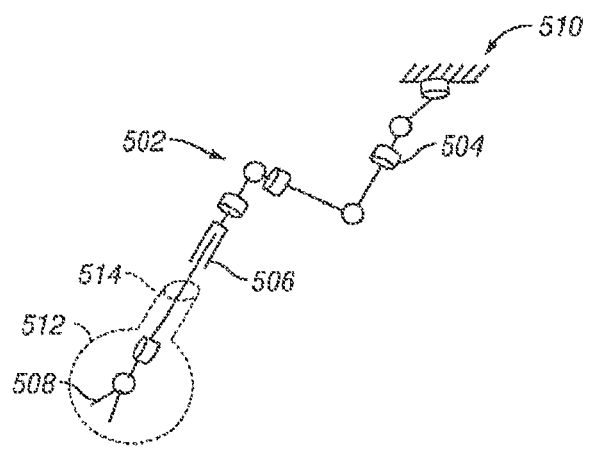
FIG. 7A schematically illustrates a manipulator assembly inserted through an aperture.
Figure 7B:
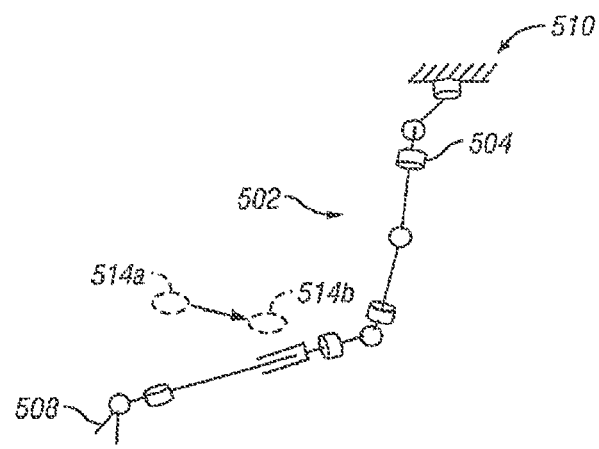
FIG. 7B schematically illustrates some of the challenges in manually repositioning the highly configurable manipulator assembly of FIG. 7A to a new aperture position.
Figure 7C:
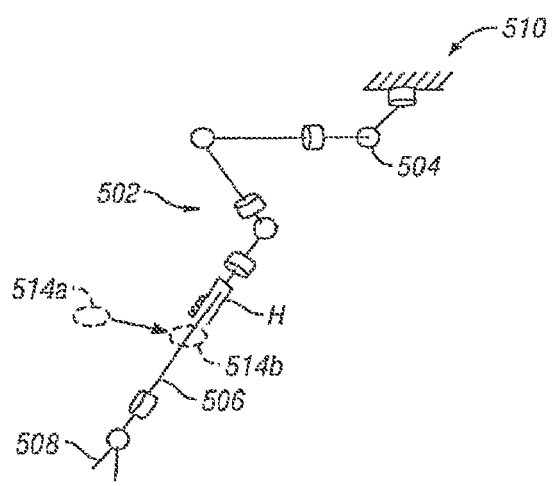
FIG. 7C schematically illustrates reconfiguring of the arm of FIG. 7A so as to enhance range of motion or the like during manual repositioning of the manipulator to a new aperture position.

Referring now to FIGS. 7A-7C, a manipulator assembly 502 here includes a manipulator 504 and an instrument 506 having an end effector 508. The term manipulator assembly, as used herein, may in some cases also encompass the manipulator without the instrument mounted thereon. The illustrated manipulator assembly generally extends from a proximal base 510 distally to the end effector 508, with the end effector and distal portion of the instrument being configured for insertion into an internal surgical site 512 via a minimally invasive surgical access 514. The joint structure of manipulator assembly 502 is similar to that described above regarding FIG. 6, and includes sufficient degrees of freedom so as to allow the manipulator assembly to be anywhere within a range of differing joint states for a given end effector position, even when the instrument is constrained to passage through minimally invasive aperture 514.

One of the challenges of working with the highly configurable manipulator assembly of FIG. 7A can be understood with reference to FIGS. 7A and 7B. Specifically, when the access site to a minimally invasive surgical procedure is to be changed from a first aperture location 514a to a second aperture location 514b, it will often be desirable to manually reposition some or all of the links of manipulator 502. Similarly, when initially setting up the manipulator assembly for surgery, the manipulator may be manually moved into a desired position aligned with the aperture location through which the associated instrument is to access the surgical site. However, in light of the highly configurable manipulator structure having a relatively large number of joints between (for example) base 510 and the instrument/manipulator interface (see FIG. 6), such manual positioning of the links can be challenging. Even when the manipulator structure is balanced so as to avoid gravitational effects, attempting to align each of the joints in an appropriate arrangement can be difficult for one person, time consuming, and may involve significant training and/or skill. The challenges can be even greater when the links of the manipulator are not balanced about the joints, as positioning such a highly configurable structures in an appropriate configuration to begin surgery can be a struggle due to the manipulator's arm length and its passive and limp design.

So as to facilitate setting up of the manipulator assembly 502 and/or manipulator 504 for a surgical procedure (or reconfiguring the manipulator assembly for accessing a different tissue of the patient), the controller 210 of workstation 200 (see FIG. 1A) may actively drive joints of the manipulator assembly during (and preferably in response to) manual movement of at least one joint of the manipulator. In FIG. 7C, a hand H of a system operator (optionally a surgeon, assistant, technician, or the like) manually moves a link of manipulator 504 or instrument 506 into alignment with a desired minimally invasive aperture 514b. During this movement, the processor drives joints proximal of the hand/manipulator engagement. As the manipulator will often have sufficient degrees of freedom so as to be in a range of alternative configurations, the proximal joints may be driven to a desired manipulator state without inhibiting the manual positioning of the distal portion of the manipulator assembly. Optionally, the joints may be driven so as to compensate for gravity, to inhibit momentum effects, to provide a desired (and often readily overcome) resistance to the manual movement so as to give the hand the impression of plastically deforming the manipulator structure at its joints, so as to keep the configurable linkage assembly in a desired pose, or the like. While this movement is shown in FIG. 7C as being performed with instrument 506 attached to manipulator 504, the manipulator assembly will often be manually positioned prior to attachment of instrument 506 to the manipulator.

Referring now to FIGS. 7A and 7C, moving a location of a minimally invasive access site relative to base 510 may significantly alter a desired pose or configuration of the manipulator so as to maintain a desirable range of motion, avoid singularities of the manipulator structure, and the like. Taking advantage of the large number of degrees of freedom of the manipulator assembly, the processor may reconfigure the joint states in a large variety of ways in response to the manual movement of a link and/or articulation of one or more of the manipulator assembly joints. The processor will often drive joints other than that being articulated manually, optionally in combination with driving of the manually articulated joint so as to allow the link to be moved. In some embodiments, movement of a minimally invasive access site may result from movement of the patient, optionally via movement of a table on which the patient is supported, due to physiological movement such as breathing or the like, and may optionally occur during manipulation of tissues at the internal surgical site by the end effector.

Figure 8A:
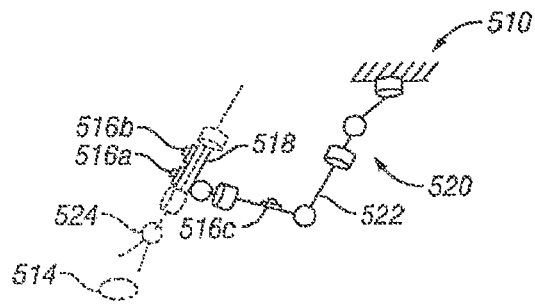
Figure 8B:
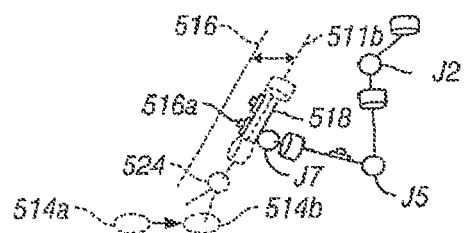
Figure 8C:
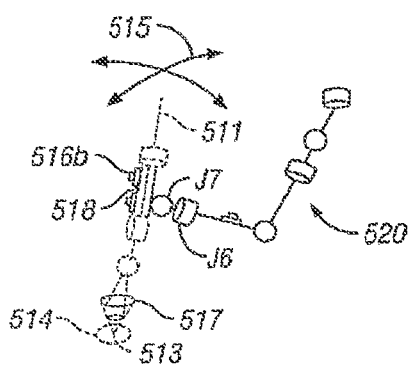
Figure 8D:
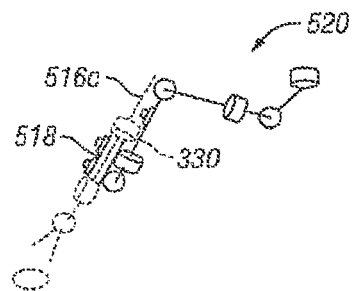
Figure 8E:
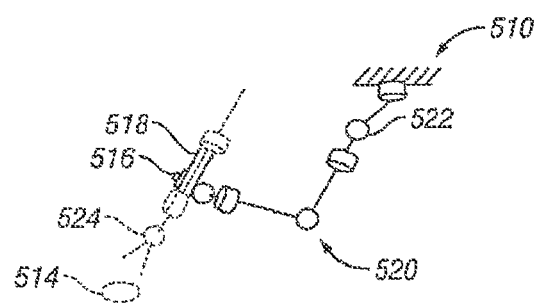
FIG. 8E schematically illustrates a highly configurable manipulator assembly having a clutch input switch so as to facilitate manual positioning of a surgical instrument adjacent a minimally invasive aperture while a processor configures the manipulator joint in response to the manual movement.

Referring now to FIG. 8E, another alternative manipulator assembly 520 includes a manipulator linkage arm 522 for removably supporting a surgical instrument 524. A port clutch input 516 comprises an input button which can be actuated by a hand engaging a link 518 of the manipulator that is to be disposed adjacent to access site 514 during surgery, such as the link to which the instrument holder is attached. This allows the hand to both actuate the input and help maneuver the manipulator into the appropriate configuration for surgery. In many embodiments, the link 518 on which port clutch input 516 is disposed will be coupleable to the shaft of the instrument by an axial insertion joint (although the instrument may not be attached at the time). In some embodiments, the hand which actuates the port clutch input 516 may be capable of repositioning the manipulator in the clutch mode without assistance from another hand. In other embodiments, repositioning of the manipulator may be facilitated by having a user position both a first hand on the manipulator link 518 adjacent port clutch input 516, and a second hand at a distance from the port clutch input, particularly when reorienting the link to a desired axial insertion angle. While port clutch input 516 is actuated by the hand, the system processor will drive joints of manipulator 520 in response to manual movement of link 518. In so doing, the processor will generally provide combinations of joint commands and/or velocities that limit the movement of the manipulator while it is in the clutch mode to one or more effective degrees of freedom. Surprisingly, coupling the joint movements together (for example, by filtering or allowing only desired linear combinations of a manually articulated joint velocity with one or more robotically driven joint velocities) can provide one or more effective clutch degrees of freedom that differ from each of the degrees of freedom of the individual joints. In most cases, more than one joint will be externally articulated, and more than one associated joint velocity command will be calculated.

Three exemplary clutch modes (and some or all of their associated effective degrees of freedom) can be understood by reference to FIGS. 8A-8D. In this embodiment of manipulator 520, three clutch inputs are shown, a port clutch input 516a and an instrument clutch input 516b mounted to link 518 adjacent the axial insertion axis of the manipulator assembly, and a pose clutch input 516c mounted along a link of the manipulator assembly between (and kinematically separated from) the base 510 and the instrument holder. Other clutch modes and combinations are also possible. The term "clutch" as used herein encompasses signal and/or data processing techniques which allow, for example, a robotic manipulator assembly to be articulated manually, often while the processor of the robotic system provides joint command signals to at least some of the joints of the manipulator assembly, and/or while an input to a master/slave controller of the processor is temporarily operationally disassociated from the manipulator assembly, either partially or fully. The terms "port clutch," "instrument clutch," and "pose clutch" broadly encompass clutching that involves or relates to an aperture (such as a minimally invasive aperture or port, or any other opening in any structure), a robotic instrument or robotic tool, and a pose or configuration of the manipulator, respectively.

As can be understood by comparing FIGS. 8A and 8B, and as generally described above, actuation of port clutch input 516a allows manipulator 520 assembly to be reconfigured manually, generally allowing a system user to manually articulate at least one joint (and typically a plurality of joints) of the manipulator assembly. In response to the manual articulation, the processor may drive one or more joints of the manipulator assembly by transmitting signals to effect desired combinations of joint velocities of the joints, with the desired combinations varying with changes in the manipulator assembly configuration. Hence, while at least one joint of the manipulator assembly is being externally articulated (typically being articulated by a user or the like, rather than the robotic controller and drive system) at least one joint of the manipulator assembly is being robotically driven. The processor can thereby maintain a desired relationship between the joint states so that at least a portion of the manipulator moves with a desired constrained movement.

In FIG. 8B, for example, the processor constrains manual movement of an instrument holder so as to translate an initial instrument shaft axis 511a to desired instrument shaft axis 511b while maintaining an orientation of the axis throughout the movement. Where, for example, the manipulator assembly is moved from alignment with first aperture site 514a to alignment with a second aperture site 514b at least in part by manual articulation of joint J2, the processor calculates coordinated movements of joints J5, J7, and the like, in response to the changing joint state of joint J2. The processor in the clutch mode calculates commands for joints J5, J7, etc. so as to provide only the desired translational movement, so that the manipulator assembly has an effective translational degree of freedom which maintains the orientation of the instrument shaft axis. The shaft axis may be translated in one, two or three degrees of freedom, and the instrument need not be mounted to the manipulator at the time the manipulator is being moved, as the instrument holder of link 518 can define the instrument axis. A variety of linkages could provide similar mechanically constrained parallel-axis motion, but in this embodiment no mechanical joint(s) of the manipulator need provide such a parallel-motion degree of freedom.

Port and other clutch modes might provide a variety of alternative clutch degrees of freedom, such as maintaining a desired pose of the manipulator assembly with ranges of motions maximized for the manipulator assembly configuration throughout translational and/or rotational movement, and the like. A variety of alternative coordinated manual and driven joint movements may be employed, with one, some, or all of the joints of the manipulator assembly being driven robotically in response to manual articulation of one, some, or all of the joints. External joint articulation may be sensed or monitored using joint state sensors of the robotic system.

Additional aspects of a port clutch mode may be provided, either instead of or in combination with those described above. For example, once the manipulator assembly is aligned with the desired aperture site, articulation of port clutch input 516a (such as by releasing the input button) can prompt the processor to identify a location of the port. Link 518 (which supports the port clutch input 516a) will often be coupleable to the instrument shaft by an axial joint, and a distal end of link 518 (and/or a cannula affixed thereto) will often be positioned at or adjacent to desired aperture site 514b. The processor can determine the location of the distal end of link 518 and or cannula from the joint states of the manipulator in response to actuation of the port clutch input 516a, and can thereafter use this information to calculate motions of the instrument shaft so that it pivots within desired aperture site 514b. Hence, the manipulator assembly in the port clutch mode can be used as an input for the aperture site location.

An exemplary instrument clutch mode can be understood with reference to FIG. 8C. Instrument clutching is useful after the manipulator assembly is aligned with the aperture site, and can facilitate manually orienting of an instrument, cannula, or other structure of the manipulator assembly toward an internal target tissue site, optionally after the cannula and/or end effector has been at least partially inserted into the patient. In response to actuation of instrument clutch input 516b, the processor drives the manipulator assembly so as to inhibit lateral movement of shaft axis 511 at a pivotal center 513 adjacent aperture site 514, while allowing lateral movement of the proximal end of link 518. For example, in response to manual articulation of joints J6 and J7, the processor may drive a combination of the manipulator joints to as to effect two-dimensional pivotal movements of link 518 centered at pivotal center 513, as schematically illustrated by arrows 515 and cone 517. In some embodiments, movement of link 518 and/or the instrument along the shaft axis may be allowed, and in other embodiments such axial movement of the instrument and/or link 518 may be inhibited. Regardless, a remote spherical center mechanical linkage may be simulated in the instrument clutch mode without limiting the movements of the manipulator assembly joints in other modes.

Yet another clutch mode, here a pose clutch mode, can be understood with reference to FIGS. 8A and 8D. In response to actuation of a pose clutch input 516c mounted to link 330 proximal of link 518, at least one joint of manipulator 520 can be articulated manually. In response, the processor drives one or more joints of the manipulator assembly so that link 518 (and its instrument holder) remains at a fixed position. As manipulator assembly 520 has a range of configurations for a given position of link 518 (and/or the instrument shaft, end effector, and the like), the processor can coordinate motions of the joints so as to keep the manipulator assembly within that range of configurations. Such a pose clutch mode could allow a system user to manually reconfigure manipulator assembly 518 from an apex downward configuration (as shown in FIG. 8A) to an apex upward configuration (as illustrated in FIG. 8D) while the processor maintains a position of a distal portion of the manipulator assembly.

Pose clutch input 516c can provide a relatively simple approach to allow manual adjustment of the pose. The system processor will often maintain the port and/or end-effector constraints when the manipulator assembly is in a pose clutch mode, but may not apply any pose constraint. Backdriveable manipulator assemblies may benefit from a gravity compensation system (hardware and/or software) while in pose clutch mode, and such a pose clutch mode may allow manual adjustment of the pose without sensing forces (for example) between the base and the cannula. In pose clutch mode, the null space could be velocity controlled, and may not be position controlled.

While exemplary clutch inputs 516a, 516b, and/or 516c may provide advantages in simplicity of implementation, ease of understanding of the various clutch modes, and the like, a variety of other clutch mode user interfaces might also be employed. For example, manipulator assemblies having systems capable of indicating forces applied to a cannula, an end effector, or the like, a buttonless haptic clutch user interface might be implemented. Rather than pushing a button to alter a mode of the processor, the user might manually articulate the manipulator assembly by applying haptic threshold-exceeding forces against appropriate structures of the manipulator assembly. The processor may counteract forces below an appropriate haptic threshold, but may treat external articulations exceeding the threshold as an input into the manipulator assembly, for example, by prioritized saturation of the end-effector, port, and/or pose constraints so that the system conforms to the external articulation.

Note that the saturation will generally not involve exceeding any hardware capabilities of the manipulator assembly, but may instead be implemented in software. For example, a processor can be configured to determine that a predetermined force threshold has been exceeded in a lateral direction on the cannula so as to indicate that complying with a change in the port location (and hence the pivotal center for future end effector movements) is appropriate. The port position could be maintained unless the forces applied at the cannula exceeds the threshold. The external articulation of the manipulator assembly might be induced by a system operator intentionally trying to change the port position, or by the patient's body wall such as when the patient moves or is repositioned on the table. In either case, if external articulation forces against the manipulator exceed the threshold value, the processor could allow the port to be moved to a new position, optionally while constraining manipulator movement to a desired port-clutch mode as described above. When forces dropped below the threshold, the processor could maintain the new port position.

A similar haptic force threshold could be applied to an instrument clutch mode, particularly given a force sensing system capable of sensing joint torques. In fact, a haptic force threshold instrument clutch could be implemented on a mechanically constrained remote pivotal center robotic system. In either case, backdriving of the manipulator using external forces exceeding the threshold would cause the processor to modify the set point of the end effector so as to maintain the new position, rather than returning the instrument to the prior position. Such instrument clutching may be most useful if implemented with a force sensing system capable of distinguishing between forces applied within the body and forces applied outside the body. Instrument clutching might then only occur if forces applied to the manipulator outside the body exceeded the threshold.

The use of haptic force thresholds or haptic wells for altering processor mode may be combined with processors configured to (typically using software code) prioritize controller tasks such as maintaining port position, end-effector position, and pose, optionally in that in priority order. Such force thresholds (and the other processor control tasks described herein) may be included in systems that implement the controller priorities using prioritized actuator torque saturation. Force thresholds may also be embodied using processors which drive manipulators according to a primary solution and a secondary control task having a priority therebetween, as described herein. Optionally, the primary priority may comprise holding the port position, and the secondary priority may comprise maintaining end-effector position. A tertiary priority may comprise maintaining pose.

Figure 9A:
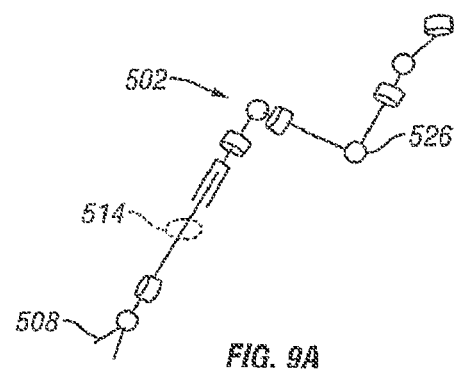
FIGS. 9A and 9B schematically illustrate robotically reconfiguring of the joints of the manipulator assembly within a range of alternative joint configurations during manual movement of the arm.
Figure 9B:
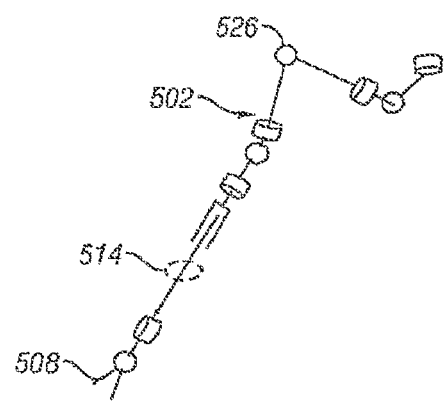

Referring now to FIGS. 9A and 9B, manipulator assembly 502 may be reconfigured by the processor for any of a variety of differing reasons. For example, a joint 526 may be driven from a downward oriented apex configuration to an upward oriented apex configuration so as to inhibit collisions with an adjacent arm, equipment, or personnel; to enhance a range of motion of the end effector 508; in response to physiological movement of the patient such as patient breathing or the like; in response to repositioning of the patient, such as by reorienting a surgical table; and the like. Some, but not all, of these changes in configuration of the manipulator assembly may be in response to external forces applied to the manipulator assembly, with the processor often driving a different joint of the manipulator than that which is being acted upon by the external force. In other cases, the processor will reconfigure the manipulator assembly in response to calculations performed by the processor. In either case, the processor may vary from a simple master-slave controller so as to drive manipulator assembly in response to a signal so as to provide a preferred manipulator assembly configuration. Such configuring of the manipulator assembly may occur during master-slave end effector movements, during manual or other reconfiguration of the manipulator assembly, and/or at least in part at a different time, such as after releasing a clutch input.

Figure 10A:
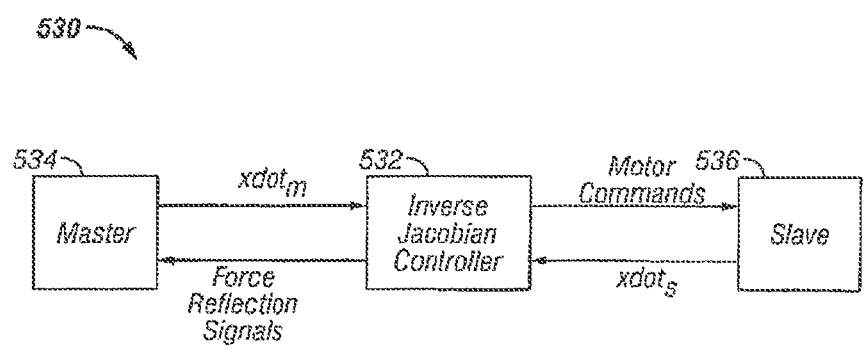
FIG. 10A is a simplified block diagram schematically illustrating a fully constrained inverse Jacobian master/slave velocity controller.

Referring now to FIG. 10A, a simplified controller schematic diagram 530 shows a master/slave controller 532 coupling a master input device 534 to a slave manipulator 536. In this and many of the other controllers described herein, the controller inputs, outputs, and computations are described using vector mathematical notation in which the vector x will often refer to a position vector in a Cartesian coordinates, and in which the vector q will reference a joint articulation configuration vector of an associated linkage (most often of the manipulator slave linkage), sometimes referred to as the linkage position in joint space. Subscripts can be appended to these vectors to identify a specific structure when ambiguity might otherwise exist, so that $x_m$ (for example) is a position of the master input device in the associated master workspace or coordinate system, while $x_s$, indicates a position of the slave in the workspace. Velocity vectors associated with the position vectors are indicated by a dot over the vector or the word "dot" between the vector and the subscript, such as $xdot_m$ or $\dot{x}_m$ for the master velocity vector, with the velocity vectors being mathematically defined as the change in the position vector with a change in time ($dx_m/dt$ for the master velocity vector example).

Figure 11:
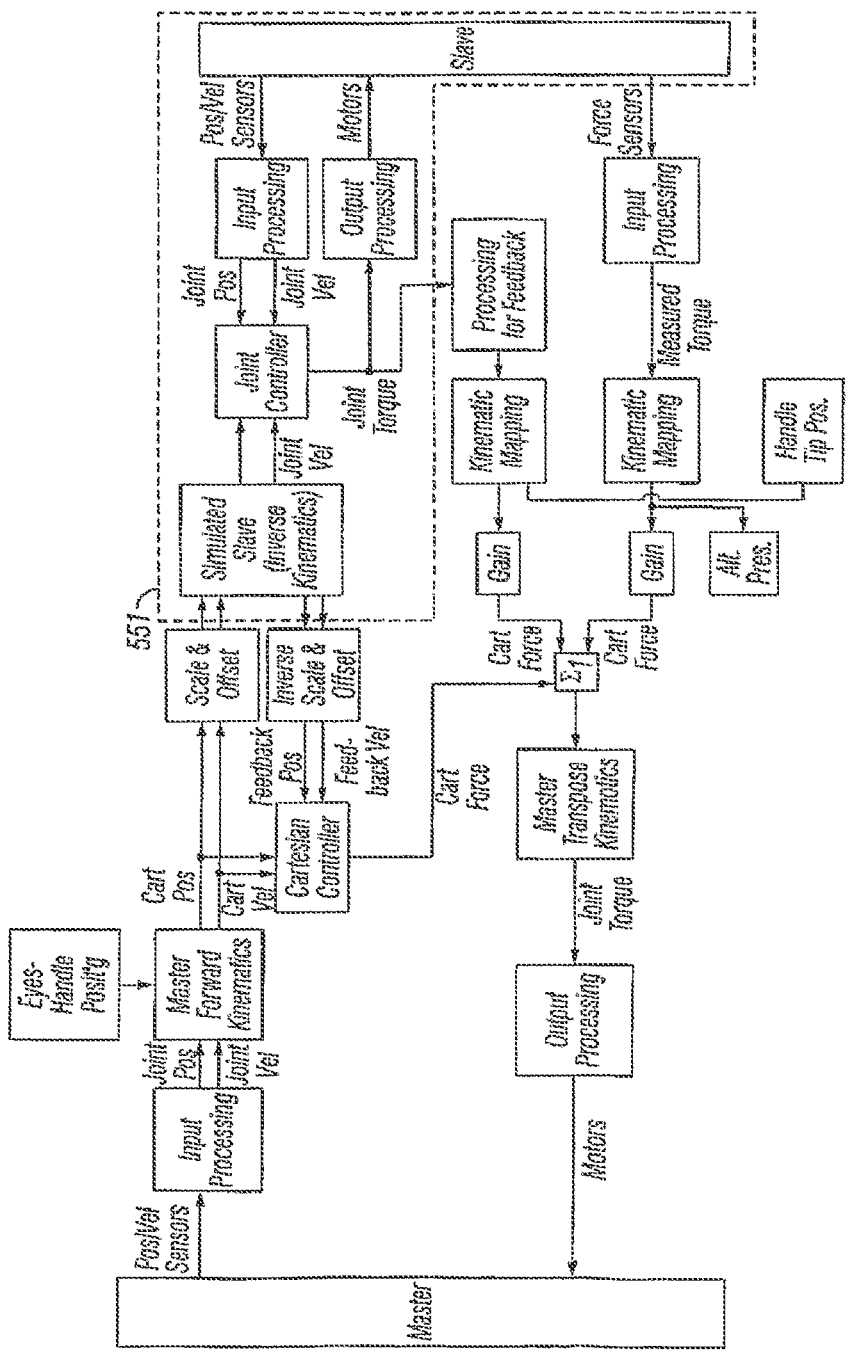
FIG. 11 schematically illustrates an exemplary inverse Jacobian controller for a fully constrained master/slave robotic surgical system.

In the embodiment of FIG. 10A, controller 532 comprises an inverse Jacobian velocity controller. Where $x_m$ is a position of the master input device and $\dot{x}_m$ is the velocity of the master input device, the controller 532 calculates motor commands for transmission to the manipulator 536 so as to effect slave end effector motions which correspond to the input device from the master velocities. Similarly, controller 532 can calculate force reflection signals to be applied to the master input device (and from there to the operator's hand) from the slave position $x_s$ and/or slave velocity $\dot{x}_s$. A number of refinements to this simple master/slave inverse Jacobian controller schematic are desirable, including those illustrated in FIG. 11 and described in detail in U.S. Pat. No. 6,424,885, the full disclosure of which is incorporated herein by reference.

Figure 10B:
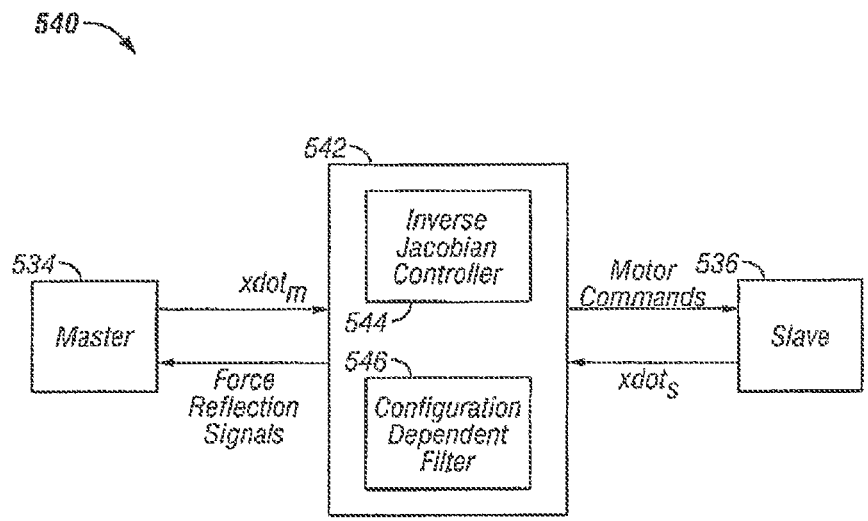
FIG. 10B is a simplified diagram of a modified master/slave controller in which an inverse Jacobian controller module is combined with a second module having a configuration dependent subspace filter so as to allow control over a manipulator which is overconstrained or underconstrained.

Referring now to FIG. 10B, a processor 542 may by characterized as including a first controller module 544 and a second controller module 546. The first module 544 may comprise a primary joint controller, such as an inverse Jacobian master-slave controller. The primary joint controller of first module 544 may be configured for generating the desired manipulator assembly movements in response to inputs from the master input device 534. However, as noted above, many of the manipulator linkages described herein have a range of alternative configurations for a given end effector position in space. As a result, a command for the end effector to assume a given position could result in a wide variety of different joint movements and configurations, some of which may be much more desirable than others. Hence, the second module 546 may be configured to help drive the manipulator assembly to a desired configuration, in some embodiments driving the manipulator toward a preferred configuration during master-slave movements. In many embodiments, second module 546 will comprise a configuration dependent filter.

In broad mathematical terms, both the primary joint controller of first module 544 and the configuration dependent filter of second module 546 may comprise filters used by processor 542 to route control authority for linear combinations of joints to the service of one or more surgical goals or tasks. If we assume that X is the space of joint motion, F(X) might be a filter giving control over the joints to i) provide a desired end effector movement, and ii) provide pivotal motion of the instrument shaft at the aperture site. Hence, the primary joint controller of first module 544 may comprise filter F(X). Conceptually, $(1-F^{-1}F)(X)$ could describe a configuration dependent subspace filter giving control actuation authority to the linear combination of joint velocities that are orthogonal to serving the goal of the primary joint controller (in this example, end effector movement and pivotal instrument shaft motion). Hence, this configuration dependent filter could be used by the second module 546 of controller 542 to service a second goal, such as maintaining a desired pose of the manipulator assembly, inhibiting collisions, or the like. Both filters may be further sub-divided into more filters corresponding to serving more specific tasks. For example, filter F(X) could be separated into $F_1(X)$ and $F_2(X)$ for control of the end effector and control of the pivotal shaft motion, respectively, either of which may be chosen as the primary or highest priority task of the processor.

While the mathematical calculations performed by the modules may (at least in part) be similar, the robotic processors and control techniques described herein will often make use of a primary joint controller configured for a first (sometimes referred to as a primary) controller task, and a configuration dependent filter which makes use of an underconstrained solution generated by the primary joint controller for a second (sometimes referred to as secondary) task. In much of the following description, the primary joint controller will be described with reference to a first module, while the configuration dependent filter will be described with reference to a second module. Additional functions (such as additional subspace filters) and or additional modules of varying priorities may also be included.

As noted elsewhere herein, the hardware and/or programming code for performing the functions described with reference to such first and second modules may be fully integrated, partially integrated, or fully separate. Controller 542 may employ the functions of the two modules simultaneously, and/or may have a plurality of differing modes in which one or both modules are used separately or in different ways. For example, in some embodiments, first module 544 might be used with little or no influence from second module 546 during master-slave manipulations, and the second module 546 having a greater role during setup of the system when the end effector is not being driven robotically, such as during port clutching or other manual articulations of the manipulator assembly. Nonetheless, in many embodiments both modules may be active most of or all the time robotic motion is enabled. For example, by setting gains of the first module to zero, by setting $x_s$ to $x_{s,actual}$, and/or by reducing the matrix rank in the inverse Jacobian controller so that it doesn't control as much and letting the configuration dependent filter have more control authority, the influence of the first module on the state of the manipulator assembly can be reduced or eliminated so as to change a mode of processor 542 from a tissue manipulator mode to a clutch mode.

Figure 10C:
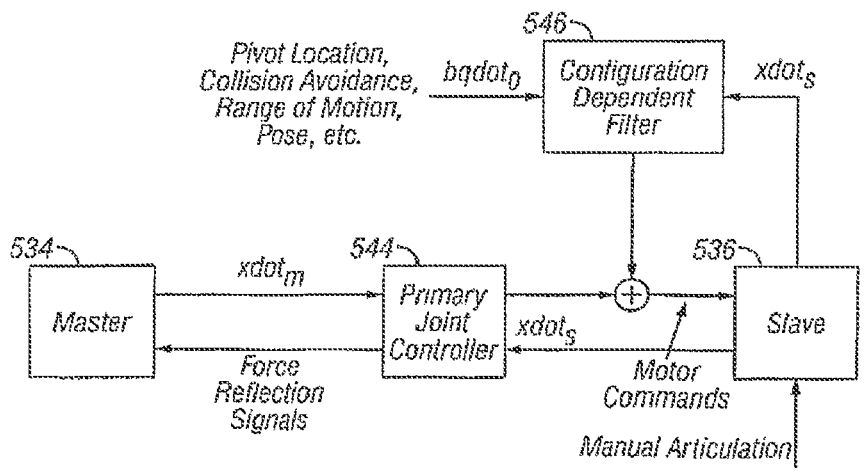
FIG. 10C illustrates a refinement of the simplified master-slave control illustrated in FIG. 10B.

FIG. 10C illustrates a refinement of the simplified master-slave control schematic 540 from FIG. 10B, and shows how different modules might be used in different processor modes. As illustrated in FIG. 10C, first module 544 may, for example, comprise some form of a Jacobian controller having a Jacobian-related matrix. Second module 546 may, in a port clutch mode, receive signals from the slave 536 indicating a position or velocity of the slave generated at least in part by manual articulation of the slave manipulator linkage. In response to this input, the second module 536 can generate motor commands appropriate for driving the joints of the slave so as to allow the manual articulation of the slave linkage while configuring the slave in the desired joint configuration. During master-slave end effector manipulation, the controller may use second module 546 to help derive motor commands based on a different signal $b\dot{q}_O$. This alternative input signal to the second module 546 of controller 542 may be used to drive the manipulator linkage so as to maintain or move the minimally invasive aperture pivot location along the manipulator structure, so as to avoid collisions between a plurality of manipulators, so as to enhance a range of motion of the manipulator structure and/or avoid singularities, so as to produce a desired pose of the manipulator, or the like. Hence, $b\dot{q}_O$ can generally comprise and/or indicate (for example) a desired set of joint velocities, more generally representing a secondary control goal, typically in joint space. In other embodiments, the processor may include separate modules and/or dependent configuration filters for clutching, secondary controller tasks, and the like Referring now to FIG. 12, a partial control schematic 550 illustrates modifications of the controller illustrated in FIG. 11. Control schematic 550 very roughly represents a modification of portion 551 of the controller of FIG. 11 to facilitate control over manipulator assemblies have large numbers of degrees of freedom. In the embodiment illustrated in FIG. 12, the first module 544 comprises an inverse Jacobian velocity controller, with the output from calculations made using an inverse Jacobian matrix modified according to a virtual slave path 552. First describing the virtual slave path, vectors associated with the virtual slave are generally indicated by a v subscript, so that a virtual slave velocity in joint space $\dot{q}_v$ is integrated to provide $q_v$, which is processed using an inverse kinematic module 554 to generate a virtual slave joint position signal $x_v$. The virtual slave position and master input command $x_m$ are combined and processed using forward kinematics 556. The use of a virtual slave (often having simplified dynamics) facilitates smooth control and force reflection when approaching hard limits of the system, when transgressing soft limits of the system, and the like, as can be more fully understood with reference to the '885 patent previously incorporated herein by reference. Similarly, calculation of motor commands such as joint torque signals or the like from joint controllers in response to the output from the inverse Jacobian matrix (as modified or augmented by the second module 546) via appropriate joint controllers, input and output processing, and the like are more fully described in the '885 patent.

Addressing the structure generally indicated by the first and second control modules 544, 546, and of the other components of control schematic 550 and other controllers described herein, these structures will often comprise data processing hardware, software, and/or firmware. Such structures will often include reprogrammable software, data, and the like, which may be embodied in machine-readable code and stored in a tangible medium for use by processor 210 of workstation 200 (see FIG. 1A). The machine-readable code may be stored in a wide variety of different configurations, including random access memory, non-volatile memory, write-once memory, magnetic recording media, optical recording media, and the like. Signals embodying the code and/or data associated therewith may be transmitted by a wide variety of communication links, including the Internet, an intranet, an Ethernet, wireless communication networks and links, electrical signals and conductors, optical fibers and networks, and the like. Processor 210 may, as illustrated in FIG. 1A, comprise one or more data processors of workstation 200, and/or may include localized data processing circuits of one or more of the manipulators, the instruments, a separate and/or remote processing structure or location, and the like, and the modules described herein may comprise (for example) a single common processor board, a plurality of separate boards, or one or more of the modules may be separated onto a plurality of boards, some of which also run some or all of the calculation of another module. Similarly, the software code of the modules may be written as a single integrated software code, the modules may each be separated into individual subroutines, or parts of the code of one module may be combined with some or all of the code of another module. Hence, the data and processing structures may include any of a wide variety of centralized or distributed data processing and/or programming architectures.

Figure 12:
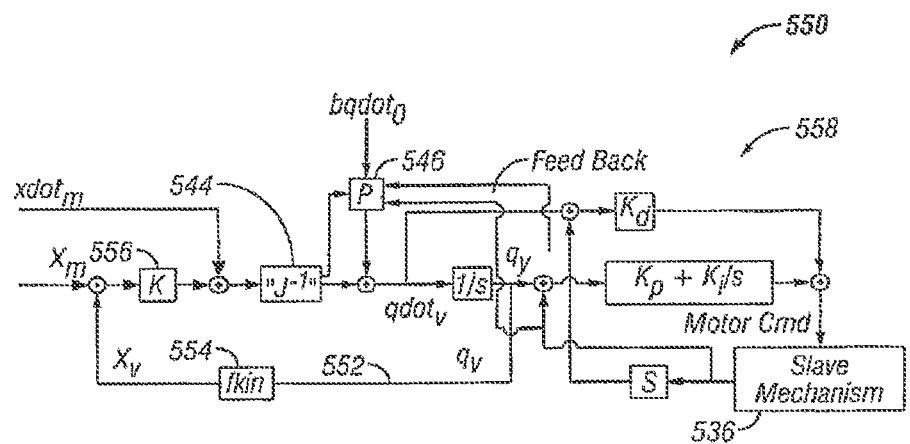
FIG. 12 schematically illustrates a modified portion of the controller of FIG. 11, in which the inverse Jacobian controller has been modified with a configuration dependent filter so that the controller respects priority of differing levels of system constraints and/or goals.

Addressing the output of the controller of FIG. 12 in more detail, the controller will often seek to solve for one particular manipulator joint configuration vector q for use in generating commands for these highly configurable slave manipulator mechanisms. As noted above, the manipulator linkages often have sufficient degrees of freedom so as to occupy a range of joint states for a given end effector state. Such structures may (but will often not) comprise linkages having true redundant degrees of freedom, that is, structures in which actuation of one joint may be directly replaced by a similar actuation of a different joint along the kinematic chain. Nonetheless, these structures are sometimes referred to as having excess, extra, or redundant degrees of freedom, with these terms (in the broad sense) generally encompassing kinematic chains in which (for example) intermediate links can move without changing the position (including both location and orientation) of an end effector.

When directing movement of highly configurable manipulators using the velocity controller of FIG. 12, the primary joint controller of the first module often seeks to determine or solve for a virtual joint velocity vector $\dot{q}_v$ that can be used to drive the joints of slave 536 in such a way that the end effector will accurately follow the master command $x_m$. However, for slave mechanisms with redundant degrees of freedom, an inverse Jacobian Matrix generally does not fully define a joint vector solution. For example, the mapping from Cartesian command $\dot{x}$ to joint motion $\dot{q}$ in a system that can occupy a range of joint states for a given end effector state is a mapping of one-to-many. In other words, because the mechanism is redundant, there are a mathematically infinite number of solutions, represented by a subspace in which the inverse lives. The controller may embody this relationship using a Jacobian matrix that has more columns than rows, mapping a plurality of joint velocities into comparatively few Cartesian velocities. Our solution $J^{-1}\dot{x}$ will often seek to undo this collapsing of the degrees of freedom of the slave mechanism into the Cartesian workspace.

The primary joint controller of the first module may employ a number of different techniques to generate such a primary solution. Mathematically, when a linear map (such as a Jacobian matrix) is many-to-one, it may be said to have a non-trivial null space, the null space typically comprising a subspace of the input space spanning one or more dimensions. For linear maps with a non-trivial null space, various pseudo inverses may be constructed to pick an acceptable inverse solution vector falling within the null space. These pseudo inverses typically have zero residual error, and the pseudo inverse solution equation can be written as $$\dot{q} = \dot{q}_{part} + \dot{q}_h$$

Here the pseudo inverse solution $\dot{q}$ is equal to the combination of any particular solution a $\dot{q}_{part}$ added to the homogeneous solution $\dot{q}_h$. Addressing the first term or particular solution, as the particular solution solves the inverse problem, we know that $$\dot{x} = J\dot{q}_{part}$$

The least-mean-squares solution, sometimes referred to as the minimum two-norm solution, is one exemplary choice for the first term of the above general joint space solution equation, as it provides one particular solution to the Jacobian. This pseudo inverse yields the final solution vector with $\|\dot{q}_{part}+\dot{q}_h\|_2$ minimized, and is among the alternative pseudo inverses described below. The second or homogeneous solution term of the above pseudo inverse solution equation is a mapping into the null space of Jacobian matrix J so that:

$$0 = J\dot{q}_h.$$

We can add any amount of $\dot{q}_h$ to $\dot{q}_{part}$ and not affect at all the motion of the mechanism regarding the control objective, $\dot{x}$. Appropriate suitable pseudo inverses will typically be designed using some sort of additional constraint to effectively determine what portion (if any) of the null space to add to a particular solution so as to fully define the solution used to calculate motor commands.

The least squares or minimum norm inverse will be indicated herein as $J^\#$. In the case where Jacobian J is underdetermined, the minimum norm inverse $J^\#$ can be identified from:

$$J^\# = J^T(JJ^T)^{-1}$$

Where $J^T$ is the transpose of the Jacobian matrix. This inverse is minimum-norm in the sense that the two-norm of the resulting solution vector $\dot{q}=J^\# \dot{x}$ is generally the smallest norm over the subspace of the solution vectors (remembering that there are in an infinite subspace of such vectors). For a surgical robot (or for any other robot), this generally corresponds to a solution that achieves the primary control objective (such as a master-slave movement of the end effector corresponding to that of a handle of the input device) with the smallest joint velocities, a reasonable goal for many robotic systems. It is also mathematically extremely convenient, being one of the easiest solutions to compute. However, this is not the only pseudo inverse of Jacobian J, and indeed there may be more appropriate task-based solutions, particularly when there are additional constraints or goals for movement of a system beyond (in our initial example) a commanded movement of the end effector with a minimum joint velocity. As the minimum norm inverse is just one example of a pseudo-inverse, where $J^{-1}$ or $J^\#$ appears herein it will often be reasonable to think of these as generally representing any pseudo-inverse, not merely the minimum norm inverse.

From the mechanisms described above, it will be understood that the desired control space $\dot{x}$ may optionally be more complex than simple end effector motion, particularly in systems in which the complexity of redundant manipulator linkages is justified. Combining of controller tasks or objectives will generally make use of a configuration dependent filter of the second module. A variety of different filters may be used. In some cases, multiple objectives may be adjoined or stacked to form an augmented desired vector, particularly if the objectives are independent. For example, in the surgical robot manipulator assembly 502 illustrated in FIG. 7*a*, we can stack or augment the commanded end effector vector with a desired cannula or pivot point location, so as to provide a software-induced center of pivotal motion at a minimally invasive aperture site. Such pivotal motion is sometimes referred to as a software center motion. Augmenting the problem statement in this manner is most easily applicable when the manipulator assembly has sufficient degrees of freedom to provide a solution to the augmented equation, as there generally are in the above-described robot manipulator assembly linkages. That is, the augmented Cartesian command vector (with the pivotal motion constraint) $\dot{q}$ still has a lower dimension than the joint velocity vector $\dot{q}$, whose dimension is typically the number of manipulator joints.

An exemplary augmented end effector and cannula control problem formulation may comprise computing a Jacobian J for each control objective. For controlling the end effector, we have $J_{\mathit{eff}}$ mapping $\dot{q}$ to $\dot{x}_{\mathit{eff}}$ where $_{\mathit{eff}}$ is here used to indicate the vector and/or matrix that is associated with the end effector. For controlling the cannula, we also construct a Jacobian $J_{can}$ that maps the joint velocities of the manipulator assembly to the cannula Cartesian velocities, written $\dot{x}_{can}$. Thus the mapping can be written:

$$\begin{bmatrix} \dot{x}_{\mathit{eff}} \\ \dot{x}_{can} \end{bmatrix} = \begin{bmatrix} J_{\mathit{eff}} \\ J_{can} \end{bmatrix} \dot{q}$$

By using the above mapping, the pseudo inverse can provide a minimum-norm solution to control both the end effector and the cannula velocities. As indicated in the control diagram of FIG. 12, position loops may be closed using signals from the manipulator assembly slave 536 to control positions (including location and orientation) as well.

Additional control objectives, such as driving toward a preferred collision-inhibiting pose or the like, may also be added in a similar manner. However, as such objectives are added the dimension of the desired vector space $\dot{x}$ may equal or surpass that of the solution space $\dot{q}$. Here, the subspace filter of the second module may take another form.

When the dimensions of the vector space and solution space are equal, the pseudo inverse should become a true inverse, and the minimum-norm pseudo inverse conveniently reduces to the true inverse. Should more augmented solutions be sought, however, the controller and the robot will not in general have sufficient degrees of freedom to satisfy all the constraints. Such a problem is described as over-constrained, so that a new kind of pseudo inverse may be created. Such a pseudo inverse attempts to compromise in some mathematical sense, returning a solution that does not perfectly satisfy all of the constraints but may still be mathematically determined to be the best solution in some identifiable sense. For example, a residual error resulting from the imperfect inverse may be computed, such as by using the minimum two-norm pseudo inverse to return a solution that minimizes the two-norm of the residual error.

Examples of additional constraints that may be added include maintaining a pose constraint, and/or avoiding a collision with an object which may be present in the workspace. In general, if a cost function C describing these or other objectives can be written in a quadratic form, we can generally state that:

$$C = r^T r = \left( \dot{x}_k - \sum_{j=1}^{n} J_{kj} \dot{q}_j \right)^2.$$

Here $\dot{x}_k$ is the desired control variable; $\dot{q}_j$ is the joint velocities of joints 1, 2, . . . n; $J_{kj}$ are the Jacobians of the desired control variable for each joint, and r is the residual error appropriate for our quadratic cost function C. The partial derivatives can generally be taken and set equal to zero, allowing us to solve for a two-norm or least squares solution:

$$\frac{\partial C}{\partial \dot{q}_j} = 0 = \frac{\partial}{\partial \dot{q}_j}\left(\dot{x}_k \sum_{j=1}^{n} J_{kj}\dot{q}_j\right)^2$$

Hence, taking partial derivatives of a quadratic cost function with the appropriate Jacobian matrix can lead to the minimum norm solution, regardless of the number of constraints. Where the system is over-constrained, the resulting solution has a minimum cost function in which the norm of r is minimized. If the system is under-constrained, the resulting solution has zero cost function and solution takes the form of the minimum two-norm solution, so that $\dot{q}_{optional} = J^T(JJ^T)^{-1}\dot{x}$.

As a simple example of an augmented controller, we can control a joint to maintain a pose using the above framework by creating a desired control variable $\dot{x}_k$ and making it identical to a selected joint $\dot{q}_j$. We then write an augmented controller as described above, but here controlling the selected joint's desired velocity to be equal to zero. The augmented Jacobian can in this example be a trivial matrix with a one in the column for the selected joint. We could then close the loop around a desired joint angle, using the block diagram of FIG. 12 in a manner similar to that of FIG. 11 while driving the selected joint toward the desired joint angle. In other words, if an embodiment of the controller of FIG. 12 were used to drive a manipulator assembly having one extra degree of freedom, but drove the extra degree of freedom to a fixed configuration, the controller would give results similar to those achieved by a fully constrained manipulator assembly driven by the controller of FIG. 11, thereby indicating that the controller of FIG. 12 is capable of performing the primary function of producing a desired end effector movement, along with the additional (if somewhat simple) task of keeping one joint fixed.

The analysis is more complex for an over-constrained system in comparison to an under-constrained system. Robots in general, and surgical robots in particular, should be designed and controlled so as to make advantageous use of all their joints. As the demands placed on the kinematic system of a robotic manipulator vary, it is not always practical or desirable to include sufficient degrees of freedom for these robotic manipulators to simultaneously perform different tasks, even if it is occasionally desirable to perform these different tasks at the same time. As a result, these systems can often be over-constrained during at least a portion of a robotic manipulation. There are several mathematical frameworks through which constraints can be added using different subspace filters. The first is augmented desired vectors, as introduced above. Some additional augmentation techniques which may be applied are discussed below, after which alternative mathematical frameworks, including at least one having advantages over augmentation, will also be described.

Along with simple combinations or augmentation of commands, a plurality of commands may optionally be combined by the controller with associated weights, for example by applying a weighted minimum norm solution. The minimum norm can be computed with respect to a set of basis vectors representing the solution space. The solution may then comprise a linear combination of those basis vectors. While basis vectors are sometimes visualized as one unit in the x direction, one unit in the y direction, etc., this is not necessarily required. For example, joints may differ significantly, with some being axial or prismatic, others being pivotal or rotational, and the like.

The use of basis vectors may be understood from a simple example, in which $e_1$ is one degree/sec for a first motor, $e_2$ is one degree/sec for a second motor, etc, and in which an initial minimum norm solution space is computed. This solution space could be arbitrarily weighted by instead choosing different basis vectors. For example, we could make $e_1$ equate to ten degrees/sec for the first motor, while $e_2$ remains one degree/sec for the second motor. A minimum norm solution will tend to make coefficients for $e_1$ no bigger, on average, than those for $e_2$ and the rest. Thus, this weighting approach can tend to make the first motor's velocity smaller, because of the weighting of basis functions we have chosen.

Further, one may chose $e_1$ to be one degree/sec in the positive direction for the first motor, and one degree/sec in the positive direction for the second motor. $e_2$ could then be one degree/sec in the positive direction for the first motor, and one degree/sec in the negative direction for the second motor. Again, we can thereby effectively change the weighting and/or the way the compromises are mapped into the space that the surgeon cares about. In general, we may wrap any transformation (it is helpful if the transformation is linear, constant, and invertible) around the optimization, as in:

$$C_{weighted} = r^T W^T W r,$$

where W is a weighting matrix, and r is the residual error. In this sense, we weight the residual error as desired, thereby helping to shape the answer.

Hence, weighting can be used to make some parts of the solution more important than others. For example, W can be made diagonal with large weights for important components and small weights for less important components of the augmented solution vector. Alternately, linear combinations of any solution components can be arbitrarily weighted.

Another technique which might be applied to derive motor commands for over constrained systems is to make use of techniques for optimization of noisy, ill-conditioned maps. All finite dimensional linear inverse problems have a condition number. This number is a measure of the skew or lopsidedness of the linear map. Technically, it is a ratio of the largest singular value of the linear map to the smallest, written $$\frac{\sigma_{max}}{\sigma_{min}}.$$

Conceptually, it describes how noise and signal interact.

If a measurement is noisy (such as the measurement of velocity of a robotic joint or a master command) and the noise is independent across joints, then it might be tempting to assume the would corrupt each solution component about equally. That is, if the desired velocity from the master, measured in the presence of noise, is $\dot{x}_{k,noise} = \dot{x}_{k,true} + GWN(\mu,\sigma)$, (where $\mu$ and $\sigma$ are the mean and variance of a Gaussian white noise process GWN, and are constant across the different Cartesian elements xdotk) then one might expect (albeit incorrectly) that $\dot{q}_{j,noise} = \dot{q}_{j,noise} + GWN(\mu,\sigma)$ in which $\mu$, $\sigma$ are also constant across the joints. In fact this is not so, and such an assumption would be in error—the additive noise is shaped by the action of the linear map, which adds some components together in a way that tends to build signal-to-noise ratio ("SNR"), and adds others in a way that tends to erode SNR. Consideration of the action of a poorly designed weighting matrix will clarify that this is possible. The measure of this effect is the condition number.

For robotic systems, the loss of precision associated with an increase in condition number happens when the Jacobian becomes ill conditioned, which in turn happens near singularities. As the condition number grows, the map acts more and more like its null space is growing by one or more dimension, but the effect is continuous, not discrete. Instead, a new subspace of joint (solution) vectors map almost to zero in the desired (master) vector space. Any noise, even round-off error in numeric calculations, can and often does result in phantom solutions, in which unrealistic joint velocities are commanded for minor velocities in command space, including minor contributions due to noise.

A number of subspace filter techniques can address this ill-conditioned map effect, including conditioning the solution by truncating the singular value decomposition ("SVD") of the Jacobian, effectively forcing the nearly grown null space to grow a full dimension. The following are brief descriptions of some of these techniques, including this SVD truncation.

One technique to address an ill-conditioned map, which may be motivated by numerical approachability as much as anything else, is to reduce the condition number in a numerically tractable manner. This technique solves a problem related to the original inverse linear problem, and can be written as:

$$J^* = J^T(JJ^T + \lambda 1)^{-1}$$

$J^*$ may be referred to as the regularized Jacobian, and $I$ is the identity matrix. The positive constant $\lambda$ is the regularization constant. It has the effect of increasing all the singular values of the linear map by a fixed amount, $\sqrt{\lambda}$. This reduces the condition number as a rising tide raises all boats: the original condition number $$\frac{\sigma_{max}}{\sigma_{min}}$$

becomes the reduced condition number $$\frac{\sigma_{max} + \sqrt{\lambda}}{\sigma_{min} + \sqrt{\lambda}}.$$

The disadvantage of the regularizing inverse is that the choice of $\lambda$ is not always well motivated physically. Further, it can change the solution for all components of the inverse, not just the ones that are swamped by noise.

Another subspace filter approach to improve the condition of an ill-conditioned map is Bayesian estimation, which is also referred to as maximum a posteriori estimation. In its simplest form it reduces to something equivalent to a regularizing inverse. The main concept is to find the free parameters $\dot{q}_j$ that maximize the a posteriori probability density function of a noisy measurement $p(\dot{q}_j, \dot{x}_1, \ldots, \dot{x}_n)$. Via Bayes' rule, we may write $$p(\dot{q}_j, \dot{x}_1, \ldots, \dot{x}_n) p(\dot{x}_1, \ldots, \dot{x}_n) = p(\dot{x}_1, \ldots, \dot{x}_n, \dot{q}_j) p(\dot{q}_j)$$

so that the optimal joint velocity vector $\tilde{\dot{q}}_j$ is obtained by $$\tilde{\dot{q}}_j = \underset{\dot{q}_j}{\operatorname{argmax}}\, p(\dot{x}_1, \ldots, \dot{x}_n, \dot{q}_j) p(\dot{q}_j)$$

Here the first of the two new probability density functions ("PDFs") is the measurement noise process, and the second is the a priori (or prior) distribution for the solution vector. It can be shown that, if the noise processes are zero mean, independent and Gaussian, and if the prior estimates on the solution are also zero mean, independent and Gaussian, then the solution may be generally written as:

$$\dot{q} = J^T(JJ^T + AA^T)^{-1}\dot{x}$$

where $A$ is a matrix formed of the variances of the measurement process divided by the variances of the prior distribution. As with a regularizing inverse, Bayesian methods change the solution. In this case, the change is physically motivated by an optimization technique meant to handle measurements in the presence of noise, and to handle the availability of prior information about the probable solution.

As a final note regarding subspace filtering of ill-conditioned maps, similar truncation methods using the singular value decomposition can be used with great effect. In particular, this approach can be applied in the control system illustrated in FIG. 11 with a six-by-six Jacobian. These methods are also extensible to the over- and under-constrained cases. One disadvantage of this approach is that the overhead of computing the inverse can be higher than other techniques discussed here, although not necessarily by much. An advantage is that the damaging condition number may be directly inspected and controlled.

A still further augmented optimization subspace filter approach which may be applied to over constrained redundant degree of freedom surgical robotic systems is constrained convex optimization. A minimum norm solution based on minimizing a quadratic form has the mathematical elegance of reducing to a system of linear equations. In general, these simultaneous linear equations may be solved rapidly and with high accuracy, and are approachable and easy to understand, and this ease of implementation certainly encourages their use. It is possible to write other optimization problem statements, including some which may be well posed and also achieve solutions almost as readily. A class of such problems is termed convex optimization, and a corresponding class of algorithms exists that yield efficient solutions, including those algorithms described by Boyd and Vandenberghe.

In addition to (or as an alternative from) the methods described above, controllers of surgical robotic systems having redundant degrees of freedom might also benefit from mathematical approaches for addressing constraints that respect priority. The above discussion has largely centered on optimization of a problem where constraints are imposed using augmented optimization. However, there may be differences in importance between a central, main control problem and any desirable, but not necessarily required solutions that we can add in. Several mathematical mechanisms are introduced below for making constraints soft, so that they fold back or can be relaxed gracefully as the main control problem gets harder, employing more of the degrees of freedom of the system. An example of a soft constraint would be to maintain an elbow or joint apex of a manipulator pointing up, as described above regarding FIGS. 5A and 5B. Another constraint might be to maximize the robot's workspace dexterity, or some other mathematical measure or robotic effectiveness. We might, for example, wish our controller to gradually abandon these secondary goals as the primary task (for example, complying with an end effector movement command vector), thereby allowing the system to achieve the primary objective at the cost of these soft, lower priority goals. For example, we might need and use the otherwise extra degrees of freedom to avoid a singularity or the like.

One way to establish a system having a plurality of constraints, tasks, or goals with priorities therebetween is to construct the secondary task as an augmented part of the solution, per the discussion above. We can then use a weighting matrix to reduce the importance of the secondary constraint as compared to that of the primary task. We can also adjust this weighting matrix during use so that the weighting is neutral when the robot is in its sweet spot, while the weighting might exert a very strong clamp on any augmented solution (making the secondary constraint contribute almost nothing to the final solution) as the difficult region was approached. It is also possible to turn on and off the weighting altogether, so as to achieve a discrete switch that respects priority. Similar techniques may be used for the regularized solution and the Bayesian approach. For example, the parameter λ, as well as the prior distribution, may be tuned in a configuration dependent manner.

An alternative mathematical approach which can allow a control system to implement a plurality of constrains wherein the constraints have a priority therebetween is sometimes referred to as the projector method. These advantageous methods generally make use of matrix projection to add constraints, and can be used instead of and/or in addition to the augmentation methods described above.

Referring once again to the block diagram of FIG. 12, projector methods may make use of input vector b$\dot{q}_0$. We may first determine that our primary constraint or task is that the master-slave movement of the end effector generated by the manipulator assembly should, as practicable, always correspond to the commanded movement of the master input device. For any linear map of this main constraint or optimization of the end effector movement, $J_{eff}$ (mapping 4 to z for the end effector) we can construct a filter for one or more other secondary constraint or command vector $\dot{q}_0$ so that this secondary constraint(s) cannot interfere with the primary commanded motion $\dot{x}_m$. This avoidance of interference between the constraints can be achieved by constructing or limiting $\dot{q}_0$ so that it is entirely within the null space of $J_{eff}$. Such a limit or filter works as a mathematical projector, projecting a general constraint or goal $\dot{q}$ into the special, prioritized goal $\dot{q}_0$ with the property $J_{eff}\dot{q}_0=0$. There are many such projectors, exactly one of which is lossless. Appropriate projectors P include the lossless projector:

$$P=1-J_{eff}^{-1}J_{eff}$$

where $J^1_{eff}$ is any pseudoinverse appropriate for use.

Now consider any task that can be written as a linear controller of rates with a position feedback, such as the remote center cannula motion task described above. The Jacobian can be formed as before, and the joint velocities responsible for achieving the task may be computed (for example) as:

$$\dot{q}_{can}=J_{can}^{\#}\dot{x}_{can}.$$

The proposed rates for the cannula task are projected so as to have no effect on the rates for the end effector tasks, and then added to the end effector task so as to generate the virtual or proposed solution:

$$\dot{q}_v=\dot{q}+P\dot{q}_{can}.$$

In general, one may write any secondary task (such as the software center motion of the manipulator) so that its projected Jacobian has authority only over those linear combinations of joints that are in the null space of the primary task (such as $J_{eff}$) by projecting the secondary task Jacobian (in our example $J_{can}$) through the projector P prior to finding the secondary task manipulator movements ($\dot{q}_{can}$). These calculations may be made recursive, and additional details regarding applicable mathematical calculation techniques have been described by Sicilliano and Slotine.

In addition to the specific projector method examples described above, similar projectors may be employed for a wide variety of uses within robotic and/or surgical master-slave controllers. The projectors developed above are powerful and may be used throughout the controller to give a directed mechanism for controlling certain degrees of freedom in certain ways. For example, to the right of "$J^{-1}$" in the block diagram of FIG. 12 is the bulk of the joint controller system 558. Using the above techniques, we could replicate that bulk, yielding two controllers with the desired or commanded velocity fed into each. Let us further filter, or project, the desired velocity according to task. We could thus create a controller for each task, each with its own set of limits, gains, saturations, and the like. In this manner it is possible to make different tasks lose priority or give up under appropriate conditions.

Still further secondary tasks may be performed using projection, augmentation, and/or other methods, including some or all of the robotic manipulations and/or set up methods described above. The generation of secondary tasks to perform collision avoidance described herein and elsewhere in the literature (see Sicilliano and Slotine and references cited thereby) can, for example, be revised so as to inhibit collisions between two simultaneously moving manipulator assemblies. One solution will use the general formalism of augmented tasks to generate rate controllers, as discussed above.

Additional modified control approaches may be implemented for other operation modes. For example, to lock an arm or manipulator assembly, or a subset of the degrees of freedom of such a structure (see clutching below), we can deliberately clamp some or all of the output vector of the first module 544 to zero. To re-establish master-slave following, we release the clamp, preferably after satisfying elementary matching conditions to rule out jump discontinuities in the input command.

Using the control algorithms described above, we can also now understand how to clutch a subset of joints or a subspace of the velocity space so as to provide an instrument clutch and/or a port clutch mode. In a minimally invasive robotic surgical system, an instrument clutch mode will generally allow manual articulation of the manipulator assembly with limited degrees of freedom. For example, when removing and replacing a first instrument with a second instrument having a different surgical end effector, an assistant may want to be able to manually move the manipulator assembly so as to advance and retract the instrument through the access site, to pivot the instrument about the access site to orient and position the new end effector, and the like. These desired clutch degrees of freedom will often not be aligned with the degrees of freedom of the mechanical joints of the system, so that simply releasing one or more joints might allow undesired or even dangerous movement of the manipulator system. Such instrument replacement clutching might be facilitated, however, if the system inhibited mathematically described motions of the manipulator assembly, such as lateral movement of a shaft or canula inserted into the access site by generating and using a projector matrix or one of the augmented solutions described above in second module 546 so as to drive one or more joints in response to manual movement of the manipulator assembly. Similarly, a port clutch mode may allow the canula or access site to be moved (and optionally to identify the new access site location when the move is completed), but may maintain an orientation and/or pose of some or all of the manipulator assembly during manual movement.

If the clutched degrees of freedom of the slave manipulator linkage coincide with one or more joint degrees of freedom (that is, if some joints are locked and some joints are free to move in the clutch mode), then clutching is direct: one simply turns off the controller for those joints that are free to move.

However, it will often be advantageous to clutch joints in a dependent way, where motion of one joint is linked by the controller to motion of at least one other joint so that they can be manually articulated together as a single degree of freedom. This may be achieved by driving at least one joint of a robotic manipulator assembly in response to external articulation of at least one other joint. The controller can effect this motion, which will often be different than any degree of freedom of the mechanical system, by defining any desired arbitrary linear combination of rates that can be treated as a single degree of freedom that the operator may manipulate, optionally while some or all of the other mechanical degrees of freedom remain locked. This general concept includes port clutching, instrument clutching, elbow clutching (in which an intermediate elbow is allowed to move, for example, from an upward oriented apex configuration around to a laterally oriented apex configuration while movement at the end effector remains inhibited), and other clutching modes. Normal joint-by-joint clutching falls out as a special case.

Giving one example of a controller system to effect clutching that can again be understood with reference to FIG. 12, at the beginning of the clutch, the virtual input command $x_v$ is tracking $x_m$ and the arm appears locked. As the system switches into clutch mode, we create a projector P that describes the linear combination of joint velocities that should not be free to move:

$$P_{lock} = J_{lock}^\# J_{lock}; P_{free} = 1 - P_{lock}.$$

If this projector is inserted in the path after block "544 ($J^{-1}$)" in the block diagram, then those velocities are hidden from the controller.

If such a projector is implemented while the arm is following, the arm will still attempt to follow but that linear combination of joints will not have a command. Moreover, should that linear combination of joints happen to move (as back-driven by the operator or the like), the controller will be blind to it and will not correct it.

Still further tasks or goals of the system may be implemented using the controller techniques described herein. Adaptive filtering and learning of a pivotal access site location from instrument movements are described below. Additionally, haptic constraints may be implemented using another variation on these techniques.

Regarding haptic constraints, it is often useful to provide cues to the operator during the manipulation of the slave arm via the master input device. For example, it may be desirable to indicate to the operator to keep away from suboptimal configurations that will cause controllability problems later. One simple method to provide such haptic constraints is to implement a joint limit technique. Another method is to turn on a one-sided servo whenever a threshold is crossed. This can be done using any of the projector or augmentation methods above.

A one-sided servo would often push back toward or away from a control point if the sensors indicate that the threshold is crossed and motion is further in the wrong direction. A velocity that is parallel to the boundary can be described for every point along the boundary. A dot product of the velocity vector and the threshold then indicates whether the operator is moving toward or away from the boundary, and the projection in the wrong direction is resisted. This can all be done with the above-described projector operators and a comparison with zero.

Figure 13:
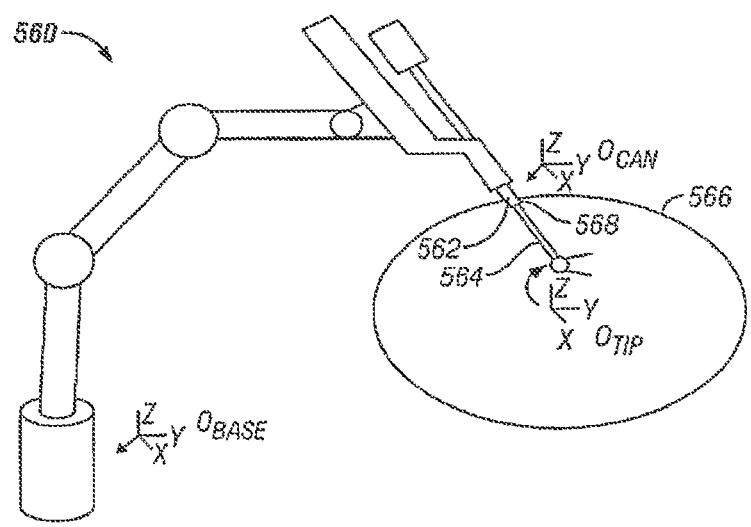
FIG. 13 schematically illustrates a slave manipulator assembly having a cannula force sensor.

Referring now to FIG. 13, a software center surgical robotic manipulator assembly 560 has particular advantages relating to movement of a pivotal center of motion 562 of a robotic instrument 564 with movement of an associated port site or minimally invasive surgical access into a patient 566. Manipulator assembly 560 may be mounted to a patient side table, ceiling mount or floor mount, and can compensate for port site motion (e.g., patient breathing) by independently controlling the location of the port site. In the exemplary embodiment of FIG. 13, the port site location can be controlled in response to Cartesian force information at the cannula pivotal center point as sensed by a force sensing cannula 568.

The coordinate frame attached to the cannula is designated Ocan in FIG. 13. This frame is distinct from a base frame, Obase, at the base of the manipulator and the tip frame, Otip, at the tip of the instrument. The Cartesian forces on the cannula can be resolved to control the position of the cannula (Ocan). The torques about Ocan are not needed for such position control. Some or all of the forces at the port can be resolved using a force sensing system of cannula 568, and/or at least some of the forces may be resolved using a force sensing system of the instrument 564, the manipulator assembly 560 (e.g., joint torque sensors of the manipulator), or the like.

Given the manipulator assembly geometry and position and sensing of Cannula forces, control laws can move the cannula position in response to reaction forces at the cannula. One example of such a control law is to set a commanded cannula Cartesian force to zero. The controller will then try to move the manipulator assembly such that the resulting Cartesian force on the cannula is minimized. It is also possible to set a nonzero commanded cannula force, e.g., 5 lbs in the positive Z cannula direction to have the arm help retract the cannula from the patient. This can also be achieved using the same controller.

Figure 13A:
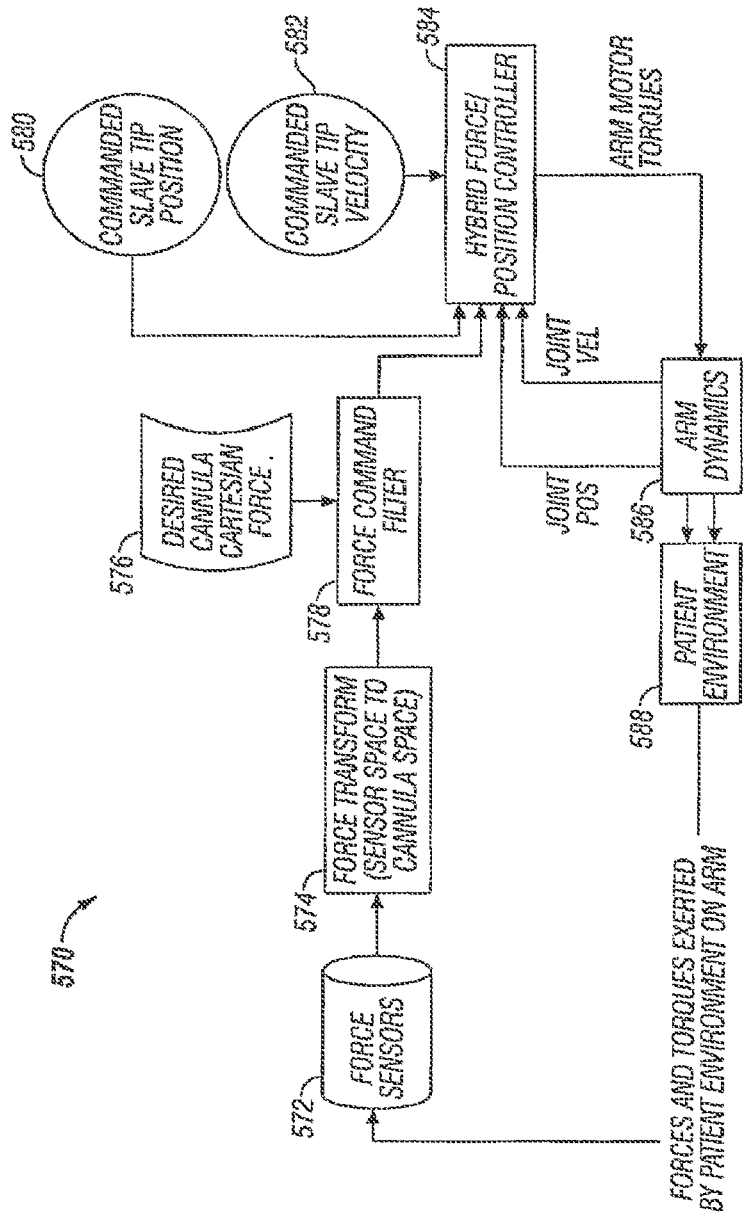
FIG. 13A schematically illustrates a hybrid force/position controller for use with the manipulator assembly of FIG. 13 or other manipulator systems described herein.

A representative controller 570 for driving the manipulator assembly 560 in response to motion of the minimally invasive access site is shown in FIGS. 13A-13C. FIG. 13A shows the overall block diagram for the cannula motion controller as it would fit into an overall software center tele-operation controller. Signals from force sensors 572 can be derived from the sensor characteristics and their placement in the arm. A transform module 574 (typically a Jacobian operator) transforms measured force sensor information into the reference frame of Cartesian cannula forces. The commanded cannula force 576 can be provided parametrically (e.g., as a programmed value). In the case of breathing compensation, this commanded force might, for example, be zero (fx=0, fy=0, fz=0). In the case of retraction, it might be (fx=0, fy=0, fz=a) where a is a retraction value (e.g., in Newtons). Filter module 578 creates a filtered error signal from the actual cannula force and the commanded cannula force. The commanded slave tip position 580 comes from the master side of the teleoperation loop (see, for example, FIG. 11) and a commanded slave tip velocity 582 may also be provided.

Hybrid controller module 584 accepts command and actual slave position and velocity signals, along with filtered cannula force error signals, and creates joint motor torque signals. The dynamics of the software center manipulator assembly are shown as 586, which interact with the dynamics of the patient environment 588.

FIGS. 13B and 13C show representative control arrangements or algorithms for filter module 578 and hybrid controller 584, respectively. In the case of the filtered force command, a simple compare module 590 can create an error signal between commanded and actual cannula force. The filtered error can then be generated by a low pass filter 592. In the case of the hybrid controller 584, a good method of control may be to convert the commanded cannula force into a commanded cannula motion 594. This can be done by creating an incremental commanded position proportional to the cannula force error and adding this incremental cannula position to the current (actual) cannula position to create a commanded cannula position. The commanded cannula position is vector assembled 596 with the commanded slave tip position, to create a command position vector for the manipulator assembly. This is combined with actual joint positions and velocities and fed into the software center slave controller 598 to create commanded motor torques, which are in turn used to drive the manipulator assembly motors.

Figure 14A:
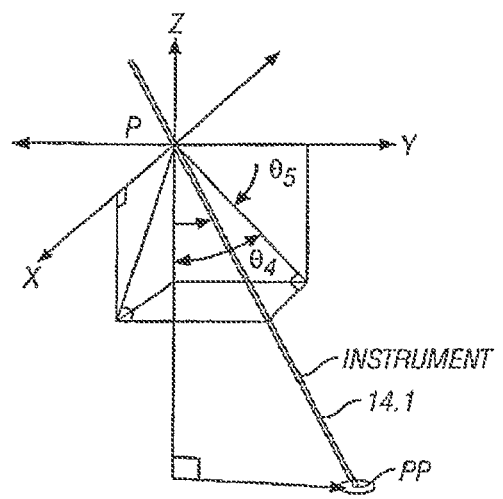
FIGS. 14A and 14B schematically illustrate an instrument coordinate frame and an instrument shaft moving pivotally about a minimally invasive access site, respectively.
Figure 14B:
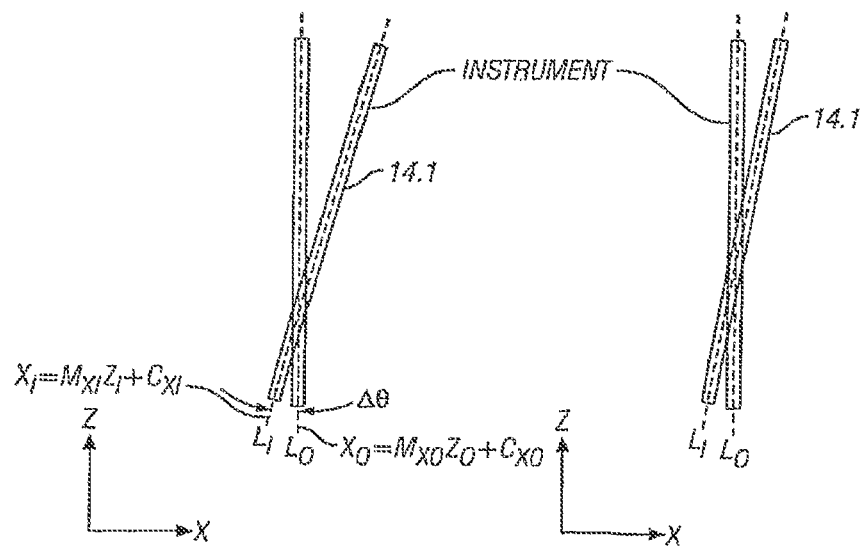

Reference is now made to FIGS. 14A and 14B which illustrate an instrument coordinate frame and an instrument shaft moving pivotally about a minimally invasive access site, respectively. As shown in FIG. 14A, pivot point PP is the position relative to the minimally invasive access port at which an instrument shaft pivots. Pivot point PP may, for example, be calculated by initially determining an original position of the interface between the manipulator instrument 14.1 and a unit vector Uo which has the same orientation as the instrument shaft. The pivot point position PP(x,y,z) values can be derived from various sensors of the manipulator assembly.

Referring to FIG. 14A the instrument can be within a first coordinate frame (x,y,z) which has the angles θ4 and θ5. The unit vector Uo can be computed by the transformation matrix:

$$U_O = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument ΔΘ can be computed by taking the arcsin of the cross-product of the first and second unit vectors Uo and U1 of the instrument in accordance with the following line equations Lo and L1.

ΔΘ=arcsin([T])

T=UoxU1 where:
T=a vector which is a cross-product of unit vectors Uo and U1.

The unit vector of the new instrument position U1 may again be determined using the position sensors and the transformation matrix described above. If the angle Δθ is greater than a threshold value, then a new pivot point may be calculated and Uo set to U1. As shown in FIG. 14B, the first and second instrument orientations can be defined by the line equations Lo and L1:

xo=Mx0·Zo+Cxo yo=Myo·Zo+Cyo      Lo x1=Mx1·Z1+Cx1 y1=My1·Z1+Cy1      L1 where:
Zo=a Z coordinate along the line Lo relative to the z axis of the first coordinate system.
Z1=a Z coordinate along the line L1 relative to the z axis of the first coordinate system.
Mxo=a slope of the line Lo as a function of Zo.
Myo=a slope of the line Lo as a function of Zo.
Mx1=a slope of the line L1 as a function of Z1.
My1=a slope of the line L1 as a function of Z1.
Cxo=a constant which represents the intersection of the line Lo and the x axis of the first coordinate system.
Cyo=a constant which represents the intersection of the line Lo and the y axis of the first coordinate system.
Cx1=a constant which represents the intersection of the line L1 and the x axis of the first coordinate system.
Cy1=a constant which represents the intersection of the line L1 and the y axis of the first coordinate system.

The slopes may be computed using the following algorithms:

Mxo=Uxo/Uzo

Myo=Uyo/Uzo

Mx1=Ux1/Uz1

My1=Uy1/Uz1

Cx0=Pox−Mx1·Poz

Cy0=Poy−My1·Poz

Cx1=P1x−Mx1·P1z

Cy1=P1y−My1P1z where:
Uo(x, y and z)=the unit vectors of the instrument in the first position within the first coordinate system.
U1(x, y and z)=the unit vectors of the instrument in the second position within the first coordinate system.
Po(x, y and z)=the coordinates of the intersection of the end effector and the instrument in the first position within the first coordinate system.
P1(x, y and z)=the coordinates of the intersection of the end effector and the instrument in the second position within the first coordinate system.

To find an approximate pivot point location PP, the pivot points of the instrument in the first orientation Lo (pivot point Ro) and in the second orientation L1 (pivot point R1) can be determined, and the distance half way between the two points Ro and R1 is computed and stored as the pivot point $R_{ave}$ of the instrument. The pivot point $R_{ave}$ is determined by using the cross-product vector T.

To find the points Ro and R1 the following equalities can be set to define a line with the same orientation as the vector T that passes through both Lo and L1.

tx=Tx/Tz ty=Ty/Tz where:
tx=the slope of a line defined by vector T relative to the Z-x plane of the first coordinate system.
ty=the slope of a line defined by vector T relative to the Z-y plane of the first coordinate system.
Tx=the x component of the vector T.
Ty=the y component of the vector T.
Tz=the z component of the vector T.

Picking two points to determine the slopes Tx, Ty and Tz (e.g. Tx=X1−xo, Ty=y1−yo and Tz=z1−z0) and substituting the line equations Lo and L1, provides a solution for the point coordinates for Ro (xo, yo, zo) and R1 (x1, y1, z1) as follows.

zo=((Mx1−tx)z1+Cx1−Cxo)/(Mxo−tx)

z1=((Cy1−Cyo)(Mxo−tx)−(Cx1−Cxo)(Myo−ty))
    ((Myo−ty)(Mx1−tx)−(My1−ty)(Mxo−tx))

yo=Myo·zo+Cyo $$y1 = My1 \cdot z1 + Cy1$$

$$xo = Mxo \cdot zo + Cxo$$

$$x1 = Mx1 \cdot z1 + Cx1$$

The average distance between the pivot points Ro and R1 can be computed with the following equation and can be stored as the pivot point of the instrument.

$$R_{ave} = ((x1+xo)/2, (y1+yo)/2, (z1+zo)/2$$

The pivot point location can be regularly continually updated with the above described calculations.

Figure 15:
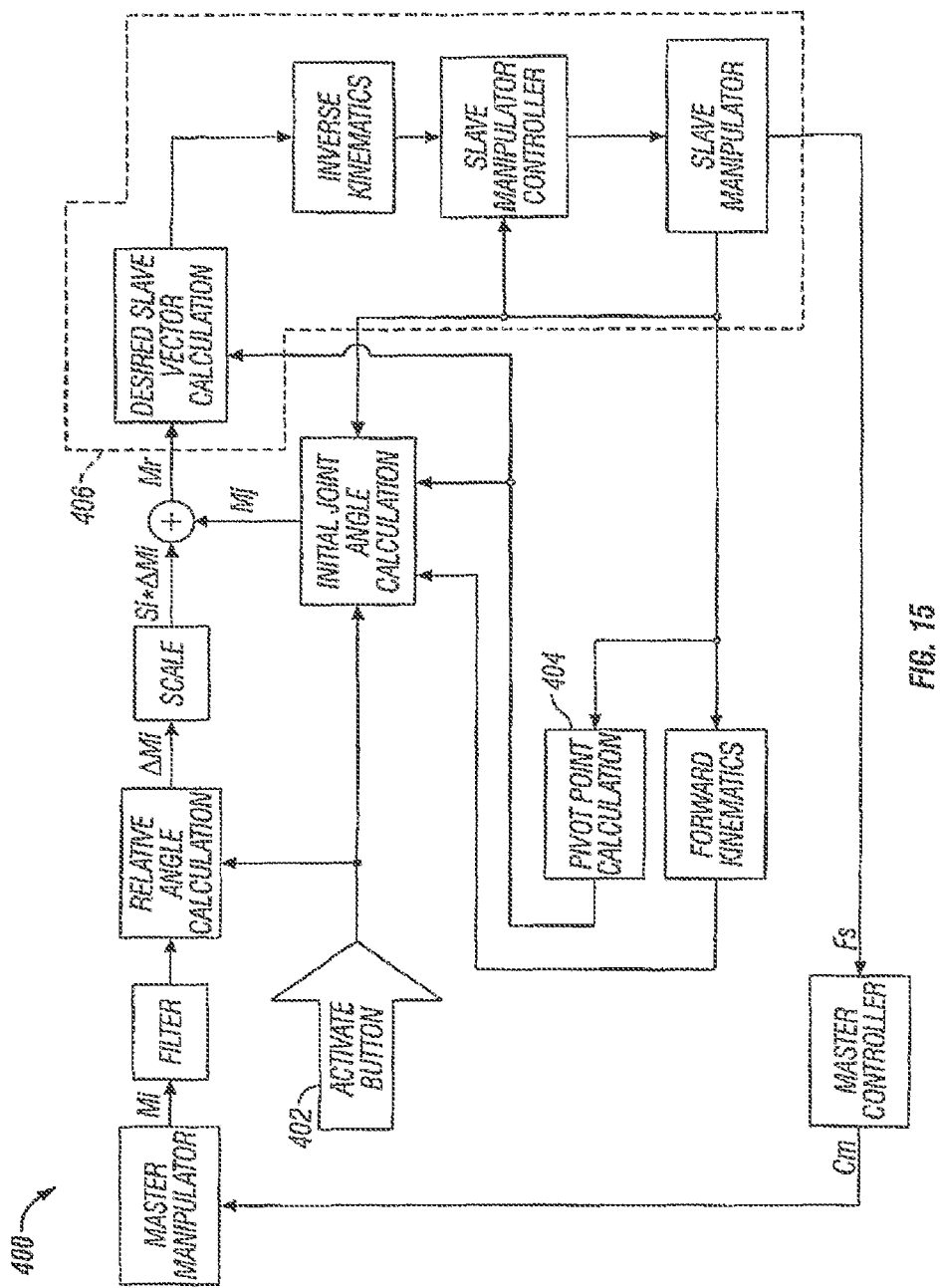
FIG. 15 is a schematic of an alternative control system of the workstation processor in which embodiment of the present invention may be implemented.

Referring now to FIGS. 14A, 14B, and 15, another control system schematic 400 illustrates how a movement of the master controller or manipulator can be used to calculate a corresponding movement of a surgical instrument so that the instrument pivots about a pivot point using an alternative controller architecture. In accordance with the control system shown in FIG. 15, the processor computes output signals for the manipulators so that the instruments move in conjunction and coordination with the movements of the master input handle. Many aspects of control system 400 are more fully described in U.S. Pat. No. 6,699,177, the full disclosure of which is incorporated herein by reference. In the control system 400 illustrated in FIG. 15, the location of a pivot point at which an instrument is inserted into an internal surgical site can be calculated by a pivot point calculation module 404 from instrument movements. The various modules shown in FIGS. 15 and 16 may again comprise hardware, software, firmware, a combination of hardware and software, or the like. The modules will often comprise data processing hardware configured to perform the calculations described herein using software, and the calculations of multiple modules may be integrated together in a common program or module, and/or the calculation of a single module may be separated into multiple programs or subroutines to be run on separate processor boards.

In short, the above descriptions enable the pivot (center) point to be determined/estimated through software. By having the capability to compute software pivot points, different modes characterized by the compliance or stiffness of the system can be selectively implemented. More particularly, different system modes over a range of pivot points/centers (i.e., ranging from one have a passive pivot point to one having a fixed/rigid pivot point) can be implemented after an estimate pivot point is computed. For example, in a fixed pivot implementation, the estimated pivot point can be compared to a desired pivot point to generate an error output which can be used to drive the instrument's pivot to the desired location. Conversely, in a passive pivot implementation, while the a desired pivot location may not be an overriding objective, an estimated pivot point can be used for error detection and consequently safety because changes in estimated pivot point locations may indicate that the patient has been moved or a sensor is malfunctioning thereby giving the system an opportunity to take corrective action.

The interaction between the moving instrument and the tissue of the minimally invasive aperture may be determined at least in part by the processor, the processor optionally allowing the compliance or stiffness of the system to be changed throughout a range extending from a passive pivot point to a fixed pivot point. At the passive end of the passive/rigid range, the proximal end of the instrument may be moved in space while the motors of the instrument holder wrist joint apply little or no torque, so that the instrument acts effectively like it is coupled to the manipulator or robotic arm by a pair of passive joints. In this mode, the interaction between the instrument shaft and the tissue along the minimally invasive aperture induces the pivotal motion of the instrument about the pivot point PP. If the surgical instrument was not inserted into the minimally invasive aperture or otherwise constrained, it may point downward under the influence of gravity, and movement of the manipulator arm would translate the hanging instrument without pivotal motion about a site along the instrument shaft. Toward the rigid end of the passive/rigid range, the location of the minimally invasive aperture may be input or calculated as a fixed point in space. The motors associated with each joint of the kinematic chain disposed proximal of the pivot point may then drive the manipulator so that any lateral force laterally against the shaft at the calculate pivot point results in a reaction force to keep the shaft through the pivot point. Such a system may, in some ways, behave similar to mechanically constrained remote center linkages. Many embodiments will fall between these two extremes, providing calculated motion which generally pivots at the access site, and which adapts or moves the pivotal center of motion within an acceptable range when the tissue along the minimally invasive access site moves, without imposing excessive lateral forces on that tissue.

It should be understood that many of the calculations described herein regarding the controller architecture of FIG. 14 may, at least in part, be interchangeable with the controller calculations described above regarding alternative control architectures. For example, a software center manipulator assembly controller such as that illustrated in FIG. 12 can leave the software center rather soft or lightly held so that the tissue forces applied by the interaction with the patient are allowed to overpower the commands sent to the manipulator motors. Such calculated saturation of the manipulator drive torques may be allowed while still controlling the end effector position to quite tight tolerances, since all motions of the manipulator assembly can be determined from the sensors of the manipulator. Several mechanisms may be applied for gradually increasing the stiffness of the software center control, including the weighted augmentation solutions discussed above. By starting with a small weighting value for the remote center, and by gradually increasing those weights to be on a par with the end effector weights, one could (for example) gradually stiffen control over the pivotal center location.

The body wall and any other exogenous forces applied to the manipulator assembly can affect the motion of the pivotal center if the pivotal center is held softly by the controller. The above-described calculations for determining the remote center location can be applied if the instrument is allowed to passively pivot adjacent the interface with the manipulator, for example. As the variance of the estimates for the pivotal motion center decreases, the weighting factor or gain may be increased. Tracking of the changes in pivotal center location may allow identification of and compensation for cyclical physiological movements such as patient breathing, beating of the heart, or the like. In some embodiments, similar calculations will allow the controller to compensate for movement of the patient such as by reorienting a surgical table, repositioning a patient on the surgical table, or the like.

Figure 16:
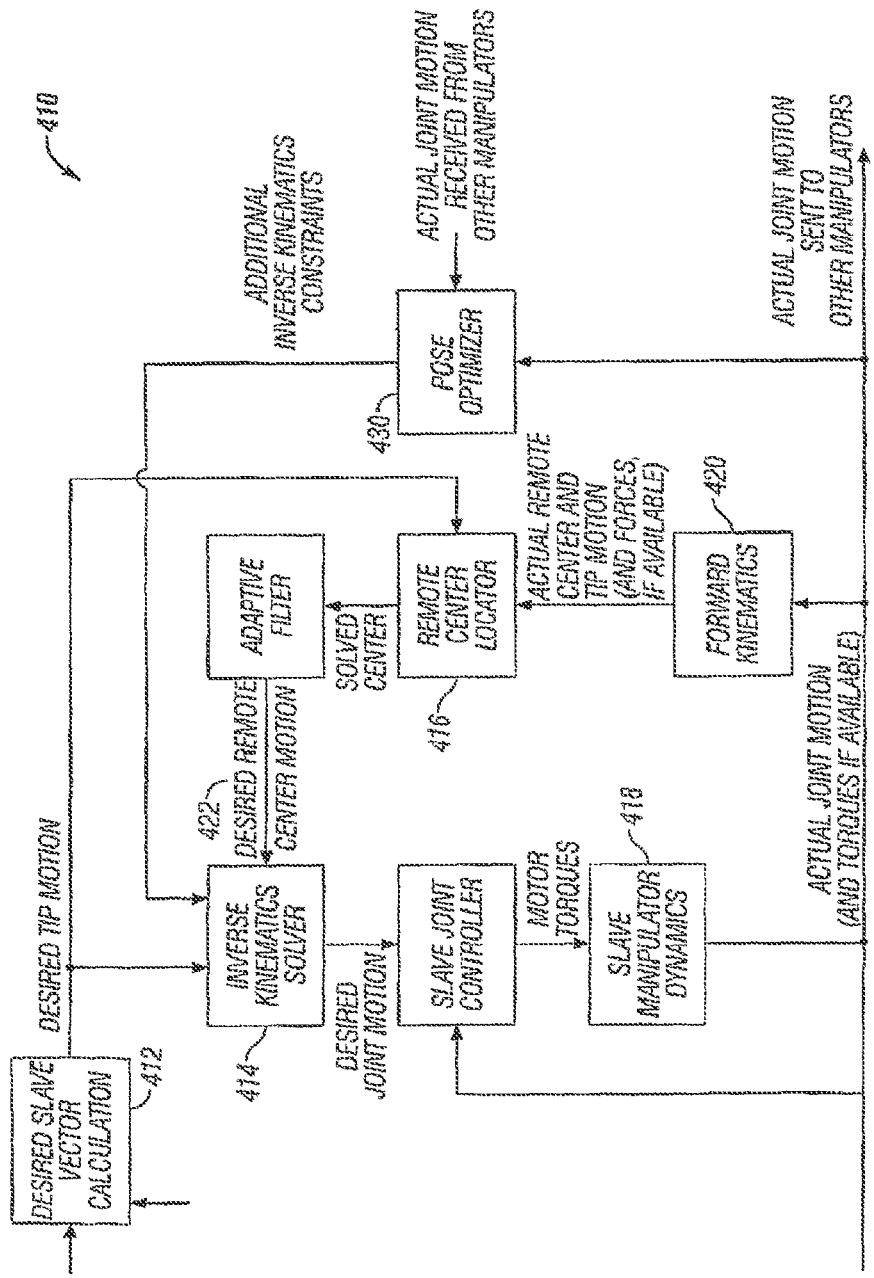
FIG. 16 schematically illustrates a modified control system with modules for solving for joint motions of manipulators having excess degrees of freedom, as suitable for modifying the system of FIG. 15 so as to implement an embodiment of the invention.

To provide a calculated pivotal motion of an instrument in space, regardless of whether or not the instrument is inserted through a minimally invasive aperture, the systems described herein may optionally include a modified manipulator command module 406 of controller 400 having a software center joint command calculation module 410 as illustrated in FIG. 16. Software center module 410 of processor 210 receives an input command corresponding to a desired end effector motion, typically in the form of signal generated in response to a master input handle movement. Software center module 410 calculates the desired corresponding end effector movement or vector at calculation module 412, optionally using coordinate system transformations such as those described in U.S. Pat. Nos. 6,424,885 and/or 6,699,177. The desired end effector movement is then transmitted to an inverse kinematics solver 414. The desired end effector motion is also used by a remote center locator 416 so as to generate a solved center about which the instrument will pivot.

Along with the desired end effector motion, the remote center locator 416 makes use of actual joint motion information from the slave manipulator 418. The information from manipulator 418 may comprise actual joint motions from prior end effector movements. The data may originate in the form of positions of each of the individual joints from potentiometers or the like, discrete steps of the individual joints from encoders or the like, or a wide variety of alternative motion indicators. Optionally, joint torques as detected at the joints of the manipulator may also be provided, and both joint positions and joint velocities may be transmitted to a forward kinematics module 420. The forward kinematics module 420 can calculate an observed minimally invasive aperture pivotal center location from the behavior of the slave manipulator during prior movements of the instrument.

Along with motion about a pivot point, the software center module 410 may also determine forces associated with the pivoting about the minimally invasive aperture, properties of the tissue tract (for example, the lateral or pivotal spring forces applied by the tissue tract to the instrument during movement of the instrument shaft and/or any lateral movement of the patient anatomy adjacent the aperture) and the like. Still further, properties of the observed pivotal center may also be determined. For example, the software center module 410 may determine any cyclical movements of the observed pivotal center with a physiological activity such as breathing or beating of the heart. Shifting of the pivotal center with changing pivotal angles or orientations may also be identified. For example, intercostal access to the chest cavity may result in a first pivotal center when a instrument inserted between the ribs is pivoted generally across the rib orientation, and a slightly different pivotal center when the instrument is angled along the lengths of the adjacent ribs. Tissue stiffness may also vary along the axis of the tissue tract and/or at differing distances from the tissue tract, so that pivoting of a shaft inserted through a minimally invasive aperture at a relatively small angle may result in a pivotal center which is disposed at a first point along a tissue tract extending through the abdominal wall, while increasing the angle of the shaft inserted through the same tract may shift the pivotal center axially along the tissue tract either proximally or distally.

The observed pivotal center information from the forward kinematics module 420 (along with any associated forces) may be combined with the commanded end effector motion from desired end effector calculation module 412 so as to generate a solved or desired center of the desired motion. The observed pivotal center and commanded tip motion may be combined using an adaptive filter, and the input to the inverse kinematic solver from the combination of the observed pivotal center and the commanded end effector motion may comprise a desired remote center motion 422.

In general, manipulator linkages which are not easily back driven will tend to keep a remote center location at a calculated position. Assuming the drive system of the linkage is not overpowered, the observed remote center will remain within a close proximity to the desired or calculated remote center location, with the difference between the observed center and desired center often falling within a relatively small servo error of the manipulator. However, the system may determine that the remote center should be removed to alleviate forces and/or torques applied to the manipulator structure. For example, the forces and/or torques may be applied to and measured at the cannula, for example, by reactive forces of the tissue against the cannula, by physiological movement of the patient during breathing or patient repositioning, or the like. In some embodiments, an operator may manually push on the arm to move the remote center to a new location, optionally before, during, or after transmitting a pivot center repositioning signal to the processor, such as by pushing a port clutch button. As described above, a large number of computational methods may be used to choose a new remote center based on the data provided by such manual movement of the manipulator linkage. The output of such calculations may be termed a solved center or a desired center, and will often represent an input from a system user to the processor, optionally by releasing the port clutch input when the appropriate structure along the kinematic chain of the manipulator assembly (such as a cannula) is disposed at the desired access site location.

In more easily back driven arms, a solved center or desired center may simply be a filtered version of an observed center. Such back drivable linkages lend themselves more directly to observing actual motions of the remote center and adjusting the control appropriately. As stronger or less back drivable manipulator linkages will tend to exhibit little motion of the observed center, employing a torque or force sensor to measure disturbance forces acting on the arm at the pivot center (such as a cannula force sensor) may facilitate such pivot location movement, rather than relying solely on joint torque or position measurements.

As described above, the shaft of the instrument between the end effector and the proximal instrument housing will typically extend through the minimally invasive aperture. The motion of this intermediate portion of the instrument will be calculated so that the instrument does not impose injury on the patient, but instead remains within the minimally invasive access site. Along with pivotal motion of the instrument shaft, the instrument may rotate about its shaft, and the shaft may be inserted distally or withdrawn proximally along the shaft axis.

So as to allow inverse kinematic solver 414 to calculate the joint motions to effect the commanded end effector movement while maintaining the instrument within the minimally invasive aperture site, the vector of the commanded Cartesian velocities and angular velocities of the tip of end effector may be provided from the slave vector calculator 414, the exemplary end effector vector comprising a 1×6 vector, with actuation of grip on end effector often being handled separately from the inverse kinematic computations. The desired remote center motion 422 input into the inverse kinematic solver may comprise a vector of Cartesian velocities of the pivotal center, such as a 1×3 vector. Algorithms that compute movement of the pivotal center (for example, based on measuring of forces at the pivotal center of a high impedance or rigidly driven arm) or the effective location of a pivotal center (based on observed pivotal motions using a low impedance or more passively pivoting arm) can be adjusted using these vector inputs. Hence, inverse kinematic solver 414 can be used for manipulator structures which are a combination of a compliant or passive rotational center and a more rigidly calculated rotational center.

As noted above, the manipulator/instrument linkages often have a greater number of degrees of freedom than the end effector has in the surgical workspace. Inverse kinematic solver 414 may nonetheless make use of controller schemes similar to those of more constrained mechanical systems, such as those described in U.S. Pat. No. 6,493,608, the full disclosure of which is incorporated herein by reference. More specifically, the use of modified inverse kinematics with a feedback tuned to correct for integrator drift may have some benefits for the joint motion calculator 410 of FIG. 16. However, certain modifications to the inverse kinematic solver 414 may be employed to adapt the joint calculator for use with a larger number of degrees of freedom and/or for the use of a calculated remote center.

Figure 17:
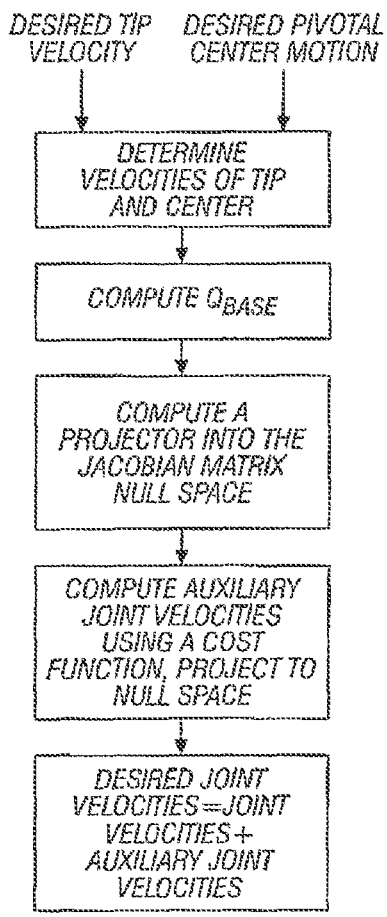
FIG. 17 schematically illustrates an inverse kinematic solution calculation as performed in one or more control module of FIG. 16.

Exemplary calculations performed by inverse kinematic solver 414 are illustrated in more detail in FIG. 17. Using the desired end effector motion and the desired pivotal center motion, inverse kinematic solver 414 first determines velocities of the instrument. In the exemplary embodiment the velocities will include a vector of the desired Cartesian velocities of the end effector, the desired angular velocities of the end effector, and the Cartesian velocities of the pivotal center, often in the form of a 1×9 vector V. From this vector, the vector of joint velocities that will cause the end effector tip and the intermediate instrument shaft adjacent the aperture to achieve the desired Cartesian and angular velocities, $\dot{q}_{base}$) may be computed as follows:

$$\dot{q}_{base} = W^{-1}J^T(JW^{-1}J^T)^{-1}V$$

in which W is a weighting matrix and J is the Jacobian matrix. For the exemplary kinematic chain illustrated in FIG. 6, the Jacobian matrix is a 9×10 matrix.

The exemplary arms will again often include more degrees of freedom than the combination of the degrees of freedom of the end effector in space (often 6) and the constraint of maintaining the instrument shaft at the aperture (3), so that they are underconstrained for the end effector and shaft pivoting tasks. Hence, these linkage systems may have more than 10 degrees of freedom, and their kinematic chains often define a null space or range of alternative configurations and/or joint velocities which the kinematic chain can have for a given end effector position. A projector vector P into the null space of the Jacobian matrix can be calculated as follows:

$$P = (I - J_{rpi} * J)$$

in which I is the identity matrix and $J_{rpi}$ is the right pseudo inverse of the Jacobian matrix.

A desired set of auxiliary joint velocities $q_{aux}$ that minimizes one or more cost functions can then be computed, with the cost function often having a configuration which drives the manipulator away from joint range-of-motion limitations, away from singularities, free from obstacles, and the like. These auxiliary joint velocities can then be projected into the null space of the Jacobian matrix. The final velocity vector may then be calculated by adding the base and auxiliary joint velocity vectors together as follows:

$$\dot{q} = \dot{q}_{base} + P * \dot{q}_{aux}$$

Referring once again to FIG. 9, kinematic solver 414 can calculate the joint motions based at least in part on information regarding the motions of other manipulators. In the exemplary embodiment, a pose optimizer module 430 receives actual joint motion data from the manipulator, and also receives actual joint motion information from the other manipulators. Based on the motions of the manipulators, the pose optimizer calculates additional inverse kinematic constraints to be input into the inverse kinematic solver 414. The pose optimizer may again drive the joint configuration of the kinematic chain using a goal function, such as to enhance separation between adjacent manipulators while effecting the commanded movement of the end effector, and while also maintaining an intermediate portion of the instrument within a minimally invasive aperture site. Pose optimizer 430 thereby takes advantage of the excess degrees of freedom of the kinematic linkage (beyond those of the end effector in the surgical site), as can be understood with reference to FIGS. 5A and 5B.

Figure 5A:
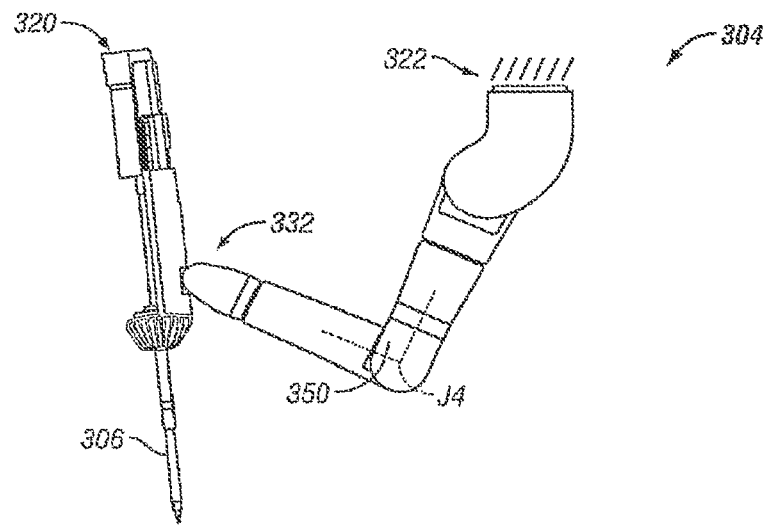
FIGS. 5A and 5B are side views of the manipulator of FIGS. 4A-C, and illustrate a downwardly oriented elbow joint configuration and an upwardly oriented elbow joint configuration of the manipulator for a given end effector position.

In FIG. 5A, manipulator 304 holds instrument 306 at a given location in space. An intermediate joint J4 of the manipulator is configured so that the axes of the links coupled together at joint J4 generally define a downward oriented apex 350. As manipulator 304 is pivotally mounted to the base at a first pivotal joint 322, is pivotally mounted to instrument holder 320 at an instrument wrist 332, and includes a roll joint and two pivotal joints therebetween, manipulator arm can be driven from this downward apex configuration to an upward oriented apex configuration illustrated in FIG. 5B, with the upward oriented apex indicated by reference numeral 352. Note that the end effector (and in fact, the entire instrument) may be at the same location in space relative to the base supporting the manipulator when the manipulator is in either of these two configurations, and while the manipulator moves between these two configurations.

So as to maintain accurate control over the surgical instruments and avoid wear or damage to the system, it will often be advantageous to configure adjacent manipulators such that collisions between the manipulators are inhibited. For example, when two manipulators are supported by one or more bases such that the manipulator arms are adjacent to each other, and when the surgical instruments supported by the manipulators are inserted through adjacent minimally invasive apertures, having the manipulators in similar configurations may lead to configurations when the manipulators move towards each other. By instead having adjacent manipulators alternate between a downward oriented apex configuration such as that illustrated in FIG. 5A and an upward oriented apex configuration such as that illustrated in FIG. 5B, the overall configuration of the manipulator system may have fewer or no collisions.

Referring once again to FIG. 15, pose optimizer 430 and joint calculator 410 may be implemented in different embodiments for a multiple manipulator system. For example, a joint calculation and associated pose optimization may be performed individually for each manipulator motion. The calculations will be performed iteratively for each manipulator, and the joint calculations may be performed by a single program running on a single processor board, by separate programs running on dedicated processor boards, or the like. Regardless, at least some of the pose optimization program may run a pose optimization routine specifically for a single manipulator. Alternatively, a single global pose optimizer may take observed slave motion data from a plurality of manipulators, optionally from all of the manipulators in the manipulator system. From this information, a globally optimized solution for the manipulator pose may be computed. This globally optimized solution may then be used as an input for the inverse kinematic solver 414 for each of the manipulators. Still further alternatives are possible, including using inverse kinematic solver to simultaneously determine actual joint motions of all joints throughout the manipulator arms.

Figure 18A:
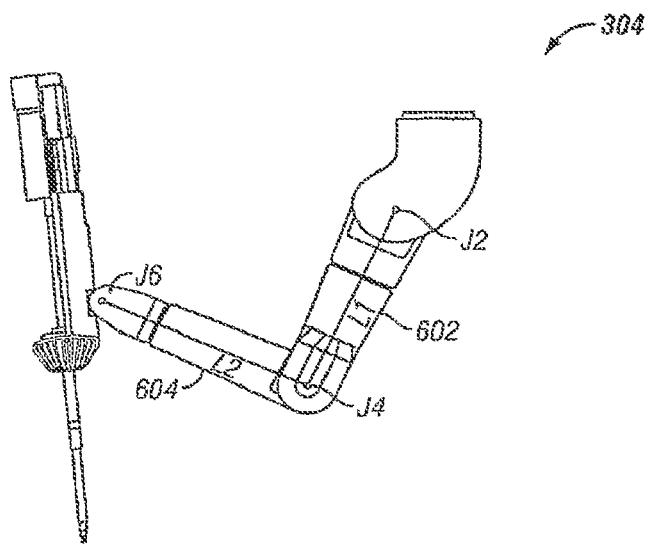
FIG. 18A illustrates exemplary linkage assembly geometry and a preferred joint configuration for the linkage assembly.

Referring now to FIG. 18A, for utility of a manipulator assembly in a multiple manipulator surgical system (see FIG. 1B, for example) each manipulator assembly should be compact and highly dexterous. Compact size enables multiple arms to share a limited space available in a vicinity of a patient while minimizing collisions between manipulator assemblies during a surgical procedure. Compact size also reduces the torque and power specifications of the motors and actuators, and helps make the system more safe for surgical staff and the patient. Compact manipulator assembly structures also tend to have lighter weight, which reduces the size of the manipulator support and setup system, and can make a manual setup process easier for a surgical staff. High dexterity generally allows the surgical end effector to be located, oriented, and moved within the patient's body in the most clinically advantageous manner.

The kinematic structure of a manipulator assembly can affect the compactness and dexterity to a significant degree. FIG. 18A illustrates an exemplary kinematic structure which provides both compactness and high dexterity. These benefits are achieved by consideration of a variety of kinematic relationships and constraints, including balancing of primary segment lengths, reducing lateral kinematic offsets, and providing at least a minimum range of motion for selected joints. These three criteria will be described in more detail in the following paragraph.

Regarding the segment for portion lengths of the manipulator assembly, and referring to FIGS. 18A, 4A-4C, 5A and 5B, and 6, the exemplary manipulator assembly 304 includes a kinematic chain of links and joints defining two arm portions. A first arm portion extends between pivotal joint J2 and pivotal joint J4 and has a length of L1. A second arm portion extends between pivotal joint J4 and pivotal joint j6 and has a length of L2. Lengths L1 and L2 of these first and second arm portions 602, 604 each extend along an associated axis of the associated arm portion, and a roll joint is present along each arm portion (see joints j3 and j5 in FIG. 6).

The useful work volume of manipulator assembly 304 is generally improved by keeping lengths L1 and L2 within about 20% of one another. If these lengths differ significantly more than that amount, volumetric holes or unreachable areas in the work volume can become problematic. Balancing lengths L1 and L2 also help to balance the angular range of motion for driving the joints J2 and J4. As the mechanical design of the joints gets significantly more complex when the range of motion increases excessively, it is generally beneficial to avoid designs involving very large ranges of motions about these pivotal joints.

Figure 18B:
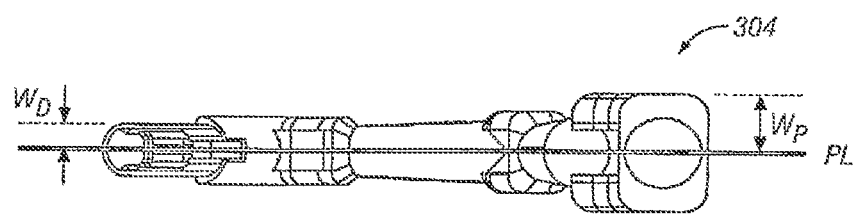
FIG. 18B is a top view of the manipulator assembly of FIG. 18A, and illustrates a planar configuration of the manipulator assembly.
Figure 18C:
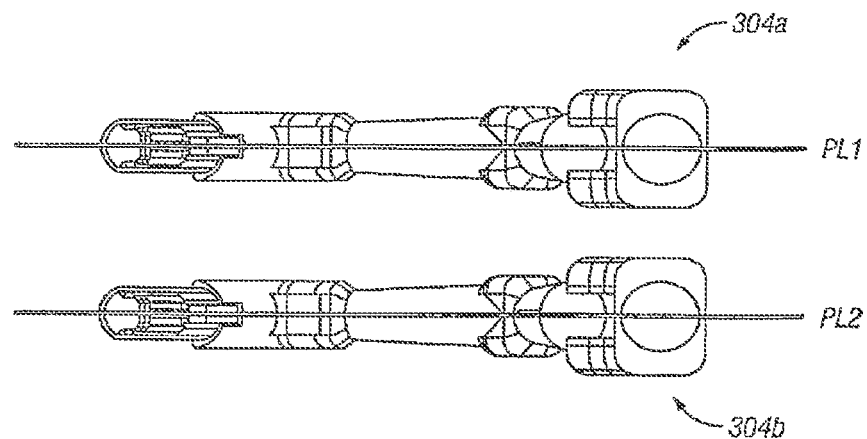
FIGS. 18C and 18D are top views illustrating planar poses for adjacent manipulator assemblies in a multi-manipulator slave system.
Figure 18D:
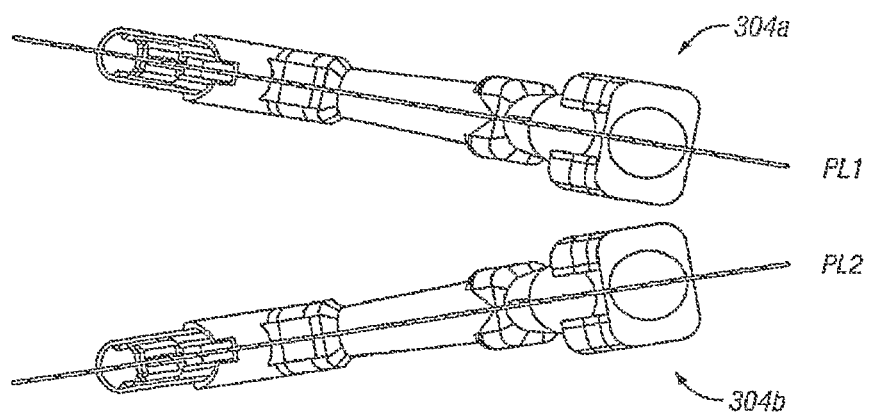

Next addressing the lateral kinematic offsets, and referring here to FIGS. 18B, 18C, and 18D, the kinematic, structural, and mechanical design of manipulator 304 as seen in these top views presents a slender profile with a limited width as measured from a central plane PL. In the exemplary embodiment a distal width $W_d$ is less than a proximal width $W_P$. Although manipulator assembly 304 will move from the planar configuration during robotic operation, it will often be advantageous to drive the linkages so as to maintain a substantially planar profile along plane PL, and/or to minimize the protrusions or widths of the arm from the central plane in a direction of an adjacent manipulator assembly. Such limiting of lateral kinematic offsets in the arm design and/or drive control logic may avoid mechanical protrusions or bumps which can potentially collide with other manipulator assemblies, the setup and manipulator support structure, the patient, surgical staff, and the like. Reducing offsets from plane PL may also help avoid holes or unreachable spaces in the arm work volume. Driving the manipulator to avoid unnecessary lateral offsets from a planar configuration can be achieved by the augmented and projector solutions described above, with this constraint or task often being lower in priority that end effector following, pivoting about the cannula, and the like.

In the exemplary embodiment illustrated in FIG. 18B (and referring to the joints and their associated axes illustrated in FIG. 6), when the arm is in a neutral pose, the pivotal axis of joint 1, the pivotal axis of joint 3, the pivotal axis of joint 5, and the linear axis of joint 7, all lie along plane PL. This condition changes as the arm moves, but in the exemplary embodiment, axes of joints J3 and J5 remain co-planar. In other words, the offsets in the kinematic chain along these joints should ideally be zero by design.

As illustrated in FIGS. 18C and 18D, the use of adjacent arms 304a and 304b which are designed for use along an associated plane PL 1 and PL2, when driven by controllers having a goal of maintaining a planar configuration of each arm at planes which are laterally and/or angularly offset, can inhibit collisions between these adjacent arms. As noted above, alternating adjacent arms between apex upward and apex downward configurations may also be employed, as described above.

Regarding the minimum ranges of motion for the joints of the manipulator assembly, range of motion may be enhanced by providing at least one of the minimum ranges of motion in the following table for the associated joint, preferably some of the ranges of motions in this table, and ideally all of the minimum ranges of motions ("ROM") in the following table:

| Joint | Min ROM |
|---|---|
| 1 | 90° |
| 2 | 135° |
| 3 | 180° |
| 4 | 180° |
| 5 | 180° |
| 6 | 90° |
| 7 | 8 inches |

Particular benefit in the overall dexterity of the highly configurable manipulator assembly 304 is provided by attention to joints J3, sometimes referred to as upper arm roll, and J6, which is sometimes referred to as wrist pitch. In many ways, the upper arm roll joint J3 can be thought of as the redundant or extra degree of freedom of the arm. Without it, manipulator assembly 304 would work very effectively in three-dimensional space. By providing this additional degree of freedom, the arm is able to attain an infinite number of poses or configurations for a given end effector position, even while the shaft of the instrument remains constrained to pivotal motion about a minimally invasive aperture. This can allow the arm to avoid obstacles, avoid collisions with other arms, and the like. This flexibility also can be used to optimize the kinematics of the manipulator linkage so as to avoid joint limits, singularities, and the like.

Figure 5B:
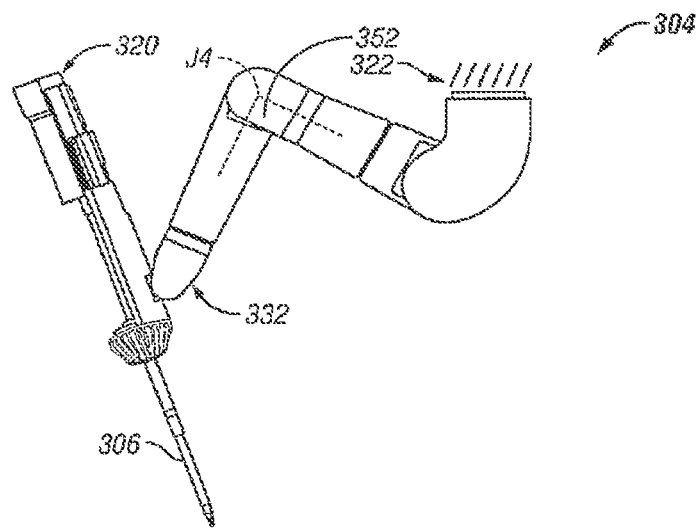

When used for robotic surgical systems having a plurality of manipulator assemblies, the manipulator linkage 304 will ideally be able to invert itself from an apex oriented downward configuration to an apex oriented upward configuration and back, as illustrated in FIGS. 5A and 5B. This can enable adjacent arms to alternate between these two configurations in primary pose (e.g., nominal starting pose), giving each arm a larger obstacle-free workspace in which to move, for example. This ability to invert the arm is facilitated by providing upper arm roll joint J3 with at least 180 degrees of travel, preferably with 360 degrees or more of travel.

Figure 18E:
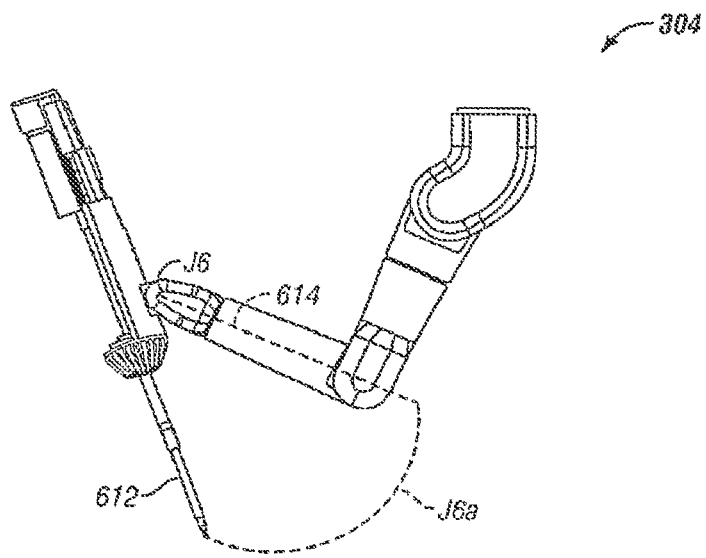
FIGS. 18E and 18F illustrate a manipulator assembly and show a desired range of motion for one of the joints of the assembly.
Figure 18F:
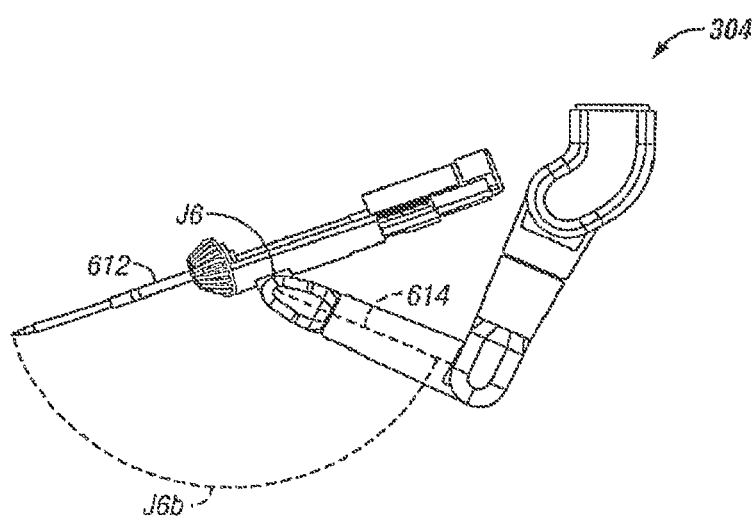

Referring now to FIGS. 18E and 18F, the ability to invert the arm between apex oriented upward and apex oriented downward configurations is also facilitated by providing the wrist pitch joint J6 with a range of motion sufficient to allow the instrument axis 612 to move quite close to the adjacent distal primary axis 614 of manipulator assembly 304, ideally in both directions. In other words, angle J6A when the end effector of the instrument is as close as possible to the apex of the manipulator arm, will preferably be 45 degrees or less, while angle J6B will preferably be 135 degrees or more when the end effector is moved as far away as possible from the apex of arm 304.

Figure 18G:
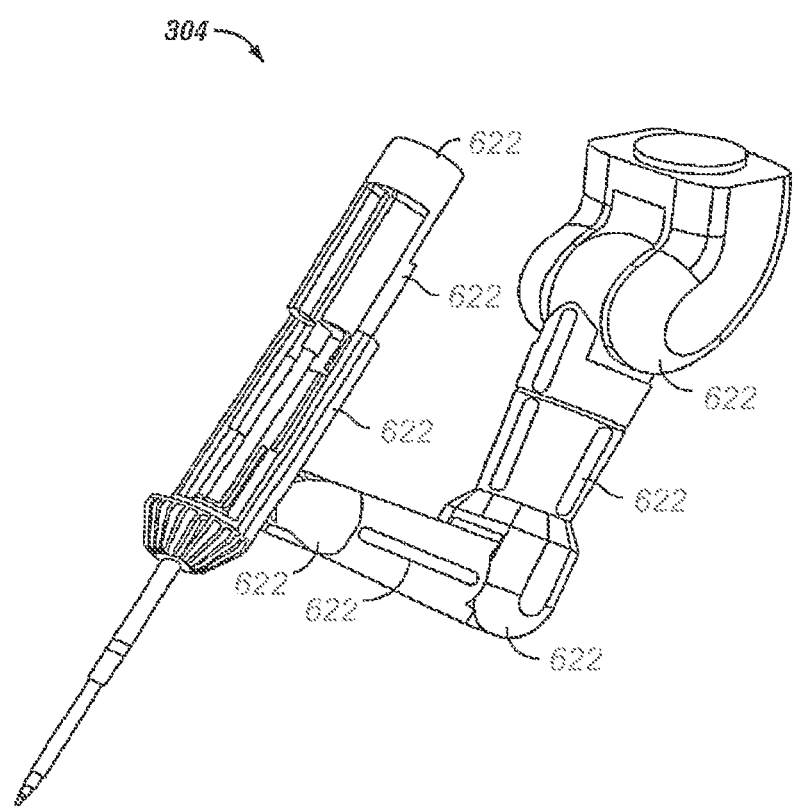
FIG. 18G is a perspective view showing an exemplary collision sensor system along a surface of a manipulator assembly.

Referring now to FIG. 18G, it may be desirable to install collision sensors 622 at one or more locations on the manipulator assembly 304. The sensors will often be disposed on the manipulator assembly's outer surfaces. The sensors may comprise contact and/or proximity sensors, and may be monitored on a real time or near real time basis by the controller. In the event of arm-to-arm contact (or near contact), the control system may take appropriate action such as driving the manipulator to a different pose, generating a soft fault, generating a hard fault, or simply generating some type of alert, such as an audible beep, a warning light, or the like to the system operator. In some embodiments, the appropriate action may depend on the location of the sensor and/or other characteristics of the collision detection signal.

Suitable collision sensors may employ tape switches such as those commercially available from Tape Switch Corporation of New York; flexible sensing arrays such as those developed by the University of Tokyo (including Takao Someya), and described in an article entitled "Flexible Sensors Make Robot Skin" in www.trnmag.com on Sep. 22/29, 2004; individual force sensing resistors or force sensing resistor arrays available commercially from Interlink Electronics; capaciflector active or passive capacitive sensing systems such as those developed by John Vranish at NASA-Goddard, or the like.

While the exemplary embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A robotic system comprising:
   a manipulator assembly configured to robotically move a distal end effector relative to a proximal base, the manipulator assembly having a linkage extending distally between the base and the end effector, the linkage having a plurality of joints, the plurality of joints being configured to provide sufficient degrees of freedom to allow a range of joint states for a position of the end effector;
   an input configured to receive a command to effect a desired movement of the end effector;
   a force sensor system configured to sense an external articulation of at least one joint of the plurality of joints, the external articulation comprising a force applied against the manipulator assembly by a tissue adjacent a minimally invasive access site in a patient; and
   a processor coupling the input to the manipulator assembly and coupled to the force sensing system, the processor being configured to determine movements of the plurality of joints in response to the command so as to move the end effector with the desired movement, the processor being further configured to drive at least one other joint of the plurality of joints in response to the external articulation sensed by the force sensor system such that the commanded desired movement of the end effector is maintained.

2. The system of claim 1, wherein the processor comprises a master-slave controller that comprises a hybrid velocity/force master-slave controller configured to effect the desired movement by calculating joint velocity commands in response to the command, joint states of the plurality of joints, and a sensed force between the manipulator assembly and the tissue.

3. The system of claim 1, further comprising:
   a cannula configured to be disposed within a minimally invasive aperture at the minimally invasive access site, the cannula being further configured to receive a shaft of the manipulator assembly therethrough, the shaft being configured to support the end effector; and
   wherein the force sensor system comprises a cannula force sensor.

4. The robotic surgical system of claim 3, wherein the processor is configured to move the minimally invasive access site in response to a force sensed by the cannula force sensor.

5. The system of claim 1, wherein the force sensor system comprises joint state sensors.

6. The system of claim 1, wherein the processor is configured to compensate for movement of the minimally invasive aperture by using the sensed external articulation, the movement of the minimally invasive access site being induced by at least one of patient breathing, patient movement, and movement of a surgical table supporting the patient.

7. The system of claim 1, wherein the processor is configured to move the minimally invasive access site in response to a force sensed by the force sensing system at the minimally invasive access site.

8. The system of claim 7,
   wherein the manipulator assembly comprises a shaft that pivots about a pivotal center adjacent a minimally invasive aperture at the access site, and
   wherein the force sensing system is configured to track changes in a location of the pivotal center, from which changes the processor is configured to identify and compensate for movement of the patient.

9. The system of claim 8, wherein the movement of the patient comprises one or more cyclical physiological movements, the cyclical physiological movements including breathing or a heartbeat of the patient.

10. The system of claim 8, wherein the processor is configured to calculate and store on a memory of the processor a location of the pivotal center and to regularly update the stored calculated location of the pivotal center.

11. The system of claim 7, wherein moving the minimally invasive access site comprises moving a surgical table that supports the patient.

12. The system of claim 8, wherein the processor comprises a master-slave controller that is configured to compensate for the movement of the patient due to one or more cyclical physiological movements.

13. The system of claim 7, wherein moving the minimally invasive access site comprises repositioning the patient on a surgical table.

14. The system of claim 8, wherein the processor comprises a master-slave controller that is configured to compensate for the movement of the patient via moving the surgical table that supports the patient or repositioning of the patient on a surgical table.

15. The robotic system of claim 1, wherein the desired movement of the end effector comprises a commanded position of the end effector.

16. The robotic system of claim 1, wherein the desired movement of the end effector comprises a commanded movement of the end effector.

17. A robotic system comprising:
   a manipulator assembly configured to robotically move a distal end effector relative to a proximal base, the manipulator assembly having a linkage extending distally between the base and the distal end effector, the linkage having a plurality of joints;

an input configured to receive commands to effect desired movements of the end effector;

a force sensor system coupled to the manipulator assembly, the force sensor system being configured to sense an external articulation of the manipulator assembly; and a processor coupling the input to the manipulator assembly and to the force sensor system, the processor being configured to determine movements of the joints in response to the command so as to move the end effector with the desired movements, the processor being further configured to conform with the external articulation of the manipulator assembly when the sensed external articulation exceeds a threshold so that at least some of the movements of the plurality of joints are determined in part in response to the threshold-exceeding external articulation, wherein the processor is configured to conform with the sensed external articulation of the manipulator assembly by driving at least one joint of the plurality of joints in response to the threshold-exceeding external articulation of another joint of the plurality of joints such that the commanded desired movements of the end effector are maintained.

18. The robotic system of claim 17:
wherein the plurality of joints is configured to provide sufficient degrees of freedom to allow a range of joint states for a position of the end effector;
wherein the threshold comprises a threshold force; and
wherein the external articulation effects at least one of:
    alignment of a manipulator shaft with an aperture pivotal center,
    configuration of the manipulator assembly in a desired pose, or
    repositioning of the end effector relative to the base.

19. The robotic system of claim 17, wherein the force sensor system is configured to determine a force applied to a shaft of the manipulator assembly by a side of an aperture along the shaft such that the threshold-exceeding external articulation comprises a sensed force between a patient and the shaft.

20. A robotic method comprising:
receiving a command from an input to effect a desired movement of a distal end effector of a manipulator assembly relative to a proximal base, the manipulator assembly comprising a linkage extending between the base and the distal end effector;

sensing an external articulation of the manipulator assembly that exceeds an articulation force threshold; and moving the distal end effector relative to the proximal base of the manipulator assembly by robotically articulating a plurality of joints of the linkage of the manipulator assembly;

wherein robotically articulating the plurality of joints comprises determining movements of the plurality of joints in response to the received command so as to move the end effector with the desired movement, and determining movements of the plurality of joints in response to the external articulation that results from exceeding the articulation force threshold by driving at least one joint of the plurality of joints in response to the threshold-exceeding external articulation of another joint of the plurality of joints such that the desired movement of the end effector according to the input command is maintained.

21. A robotic method comprising:
receiving a command from an input to effect a desired state of a distal end effector of a manipulator assembly, the manipulator assembly comprising a linkage extending between a proximal base and the distal end effector, the manipulator assembly being configured to effect the desired state of the end effector according to the received input command, the desired state being a position or motion state of the end effector relative to the base;

sensing an external articulation of a joint of a plurality of joints of the linkage of the manipulator assembly;

determining movements of the plurality of joints in response to the external articulation if the sensed external articulation exceeds an articulation force threshold; and driving at least one of the joints of the plurality of joints in response to the threshold-exceeding external articulation such that the commanded desired state of the end effector is maintained.

22. The method of claim 21:
wherein the manipulator assembly comprises a surgical instrument shaft;
wherein a pivotal center is defined along the instrument shaft; and
wherein driving at least one of the joints of the plurality of joints further comprises keeping the pivotal center stationary.

* * * * *